United States Patent
Hammock et al.

(10) Patent No.: US 10,858,338 B2
(45) Date of Patent: Dec. 8, 2020

(54) INHIBITORS FOR SOLUBLE EPOXIDE HYDROLASE (SEH) AND FATTY ACID AMIDE HYDROLASE (FAAH)

(71) Applicant: The Regents of the University of California, Oakland, CA (US)

(72) Inventors: Bruce Hammock, Davis, CA (US); Sean Kodani, Orangevale, CA (US)

(73) Assignee: The Regents of the University of California, Oakland, CA (US)

( * ) Notice: Subject to any disclaimer, the term of this patent is extended or adjusted under 35 U.S.C. 154(b) by 57 days.

(21) Appl. No.: 16/084,465

(22) PCT Filed: Mar. 14, 2017

(86) PCT No.: PCT/US2017/022335
§ 371 (c)(1),
(2) Date: Sep. 12, 2018

(87) PCT Pub. No.: WO2017/160861
PCT Pub. Date: Sep. 21, 2017

(65) Prior Publication Data
US 2019/0077785 A1    Mar. 14, 2019

Related U.S. Application Data

(60) Provisional application No. 62/308,789, filed on Mar. 15, 2016.

(51) Int. Cl.
| | |
|---|---|
| C07D 401/06 | (2006.01) |
| C07D 271/10 | (2006.01) |
| C07D 211/16 | (2006.01) |
| C07D 211/46 | (2006.01) |
| C07D 401/12 | (2006.01) |
| C07D 401/14 | (2006.01) |
| C07D 413/14 | (2006.01) |
| C07D 417/04 | (2006.01) |
| C07C 275/28 | (2006.01) |
| C07C 275/34 | (2006.01) |
| A61P 35/00 | (2006.01) |
| C07C 275/36 | (2006.01) |

(52) U.S. Cl.
CPC ............ *C07D 401/06* (2013.01); *A61P 35/00* (2018.01); *C07C 275/28* (2013.01); *C07C 275/34* (2013.01); *C07C 275/36* (2013.01); *C07D 211/16* (2013.01); *C07D 211/46* (2013.01); *C07D 271/10* (2013.01); *C07D 401/12* (2013.01); *C07D 401/14* (2013.01); *C07D 413/14* (2013.01); *C07D 417/04* (2013.01); *C07C 2601/14* (2017.05)

(58) Field of Classification Search
None
See application file for complete search history.

(56) References Cited

U.S. PATENT DOCUMENTS 8,901,111 B2 * 12/2014 Breitenbucher ..... C07D 401/12
514/161
9,029,401 B2    5/2015 Hammock et al.

FOREIGN PATENT DOCUMENTS

WO    2008016884 A2    2/2008

OTHER PUBLICATIONS

Pubchem CID 3244652; Create Date: Aug. 16, 2005; Date Accessed: May 8, 2017.
Pubchem CID 4344975; Create Date: Sep. 14, 2005; Date Accessed: May 8, 2017.
Pubchem CID 42611949; Create Date: Jun. 22, 2009; Date Accessed: May 8, 2017.
International Search Report for PCT/US02017/022335 dated Jul. 19, 2017.

* cited by examiner

*Primary Examiner* — Zinna Northington Davis
(74) *Attorney, Agent, or Firm* — Mintz Levin Cohn Ferris Glovsky and Popeo, P.C.

(57) ABSTRACT

The present invention provides compounds that are dual inhibitors of soluble epoxide hydrolase and fatty acid amide hydrolase. The present invention also provides methods of using the compounds to inhibit soluble epoxide hydrolase and fatty acid amide hydrolase, and to treat cancer.

18 Claims, 2 Drawing Sheets

INHIBITORS FOR SOLUBLE EPOXIDE HYDROLASE (SEH) AND FATTY ACID AMIDE HYDROLASE (FAAH)

CROSS-REFERENCES TO RELATED APPLICATIONS

This application claims priority to U.S. Provisional Application No. 62/308,789, filed Mar. 15, 2016, which is incorporated in its entirety for all purposes.

STATEMENT AS TO RIGHTS TO INVENTIONS MADE UNDER FEDERALLY SPONSORED RESEARCH AND DEVELOPMENT

This work was supported by Grants No. R01 ES002710 and P42 ES04699 from the National Institute of Environmental Health Sciences, and Grant No. U54 NS079202-01 from the National Institute of Health. The Federal Government has certain rights in this invention

BACKGROUND OF THE INVENTION

Soluble epoxide hydrolase (sEH) is an alpha-beta fold hydrolase responsible for the regulation of lipid epoxides including epoxyeicosatrienoic acid (EETs). These signaling molecules are responsible for mediating a number of biological processes including nociception, inflammation, and hypertension. These effects are potentially mediated through multiple signaling pathways, including PPARα, TRP channels, the $CB_2$ receptor and others. By converting the biologically active epoxides to their respective inactive diols, sEH negatively regulates the activity of these mediators. The in vivo stability of EETs and related epoxides are low due to the high catalytic efficiency of sEH; thus, sEH inhibition has been the major approach for studying the biological role of lipid epoxides. In the process, this signaling pathway has become a potential therapeutic target for numerous disease states including neuropathic and inflammatory pain and cancer. In addition to their use are experimental tools, several of these inhibitors have been developed as United States Food and Drug Administration (USFDA) Investigational New Drug (IND) candidates that have reached Phase I (GlaxoSmithKline GSK2256294) and Phase II (Arete Therpaeutics AR9821), clinical trials for the treatment of chronic obstructive pulmonary disease (COPD) and hypertension, respectively.

In addition to sEH, another enzyme that has been studied as a potential therapeutic target for neuropathic and inflammatory pain and cancer is fatty acid amide hydrolase (FAAH). This enzyme hydrolyzes the arachidonoyl ethanolamide (AEA), an endocannabinoid that regulates nociception and other physiologies through activation of the cannabinoid receptors. Similar to EETs and sEH, AEA is unstable in vivo due to its rapid metabolism by FAAH and therefore most of the in vivo studies relating to AEA have used FAAH inhibitors. Several of these inhibitors have been developed for clinical use; however, the first of these, PF-04457845, failed in Phase II clinical trials despite excellent target engagement.

Recently, it was demonstrated that concurrent inhibition of sEH and FAAH synergizes to reduce both inflammatory and neuropathic pain (Sasso et al. (2015) *Pharmacol. Res.* 97:7). In the same study, the sEH inhibitor trans-4-[4-(3-trifluoromethoxyphenyl-1-ureido)-cyclohexyloxy]-benzoic acid (t-TUCB) was identified as a weak FAAH inhibitor (human FAAH half maximal inhibitory concentration ($IC_{50}$) =260 nM). Interestingly, this compound has been used extensively in rodents to study potential therapeutic uses for sEH inhibitors, including for reducing hepatic fibrosis, smoke-induced chronic obstructive pulmonary disease and high blood pressure. t-TUCB has also been used in primate and equine (PCT International Patent Application No. WO 2013/138118) models and has been tested in veterinary clinical trials for canine and feline companion animals. The observed weak dual inhibition corresponded to a mild increase in the length of drug efficacy, but it was not apparent whether the improved efficacy occurred from dual inhibition or was due to other factors such as improved pharmacokinetics.

The ability of a dual inhibitor to demonstrate efficacy at equivalent or lower doses than a combination dosing of single-target counterparts is a very desirable property for a pharmaceutical compound. This is in part because a lower necessary dose can increase selectivity against off-target pathways and reduce unwanted side effects. As discussed above, previously available compounds have an inhibitory potency for at least one of the two targets that is too low for these therapeutic effects to be realized. In addressing this limitation, the present invention meets the need for a dual inhibitor of both sEH and FAAH as well as other needs.

BRIEF SUMMARY OF THE INVENTION

In one embodiment, the present invention provides compounds having the structure of formula J:

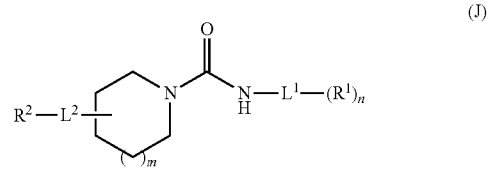

(J)

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. $L^1$ can be $C_{6-10}$ arylene or $C_{5-10}$ heteroarylene. $L^2$ is absent or $C_{1-6}$ alkylene. $R^2$ can be $C_{6-12}$ aryl or $C_{5-12}$ heteroaryl, optionally substituted with 1 to 2 $R^{2a}$ groups. Each $R^{2a}$ can independently be hydrogen, $C_{6-12}$ aryl, —O—$C_{6-12}$ aryl, $C_{5-12}$ heteroaryl or —O—$C_{5-12}$ heteroaryl, wherein the $C_{6-12}$ aryl and $C_{5-12}$ heteroaryl groups are optionally substituted with 1 to 2 $R^{2b}$ groups. Each $R^{2b}$ can independently be halogen, $C_{1-6}$ haloalkyl, $C_{1-6}$ alkoxy or $C_{1-6}$ haloalkoxy. Subscript m is 0 or 1. Subscript n is an integer from 1 to 4. When $R^2$ is quinolin-3-yl, $L^2$ is methylene, subscripts m and n are both 1, and $L^1$ is phenylene, then $R^1$ is $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$) CH$_2$C(O)O$R^{1b}$, —N($R^{1a}$)($R^{1b}$), —S(O)$_2R^{1a}$, —S(O)$_2$N ($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. The compounds of formula J can also be the pharmaceutically acceptable salts or isomers thereof.

In another embodiment, the present invention provides compounds having the structure of formula I:

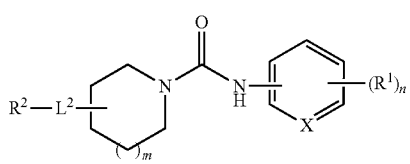

(I)

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl and $C_{5-12}$ heteroaryl. $R^{1a}$ can be hydrogen, $C_{1-6}$ alkyl, $C_{1-6}$ hydroxyalkyl, or $C_{1-6}$ alkyl-$C_{612}$ aryl. $R^{1b}$ can be hydrogen or $C_{1-6}$ alkyl. $L^2$ can be absent or $C_{1-6}$ alkylene. $R^2$ can be $C_{6-12}$ aryl or $C_{5-12}$ heteroaryl, optionally substituted with 1 to 2 $R^{2a}$ groups. Each $R^{2a}$ can independently be hydrogen, $C_{6-12}$ aryl, —O—$C_{6-12}$ aryl, $C_{5-12}$ heteroaryl or —O—$C_{5-12}$ heteroaryl, wherein the $C_{6-12}$ aryl and $C_{5-12}$ heteroaryl groups are optionally substituted with 1 to 2 $R^{2b}$ groups. Each $R^{2b}$ can independently be halogen, $C_{1-6}$ haloalkyl, $C_{1-6}$ alkoxy or $C_{1-6}$ haloalkoxy. X can be CH or N. Subscript m can be 0 or 1. Subscript n can be an integer from 1 to 4. When $R^2$ is quinolin-3-yl, $L^2$ is methylene, subscripts m and n are both 1, and X is CH, then $R^1$ is $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. The compounds of formula I can also be the pharmaceutically acceptable salts or isomers thereof.

In another embodiment, the present invention provides a method for inhibiting a soluble epoxide hydrolase and fatty acid amide hydrolase, the method including contacting the soluble epoxide hydrolase and fatty acid amide hydrolase with a therapeutically effective amount of a compound of formula I.

In another embodiment, the present invention provides a method of treating cancer, the method including administering to a subject in need of such treatment, a therapeutically effective amount of a compound of formula I.

In another embodiment, the present invention provides compounds having the structure of formula IIc:

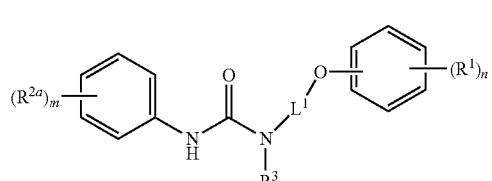

(IIc)

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl and $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. Each $R^{2a}$ can independently be hydrogen, $C_{1-6}$ alkyl, halogen, $C_{1-6}$ haloalkyl, $C_{1-6}$ alkoxy or $C_{1-6}$ haloalkoxy. $L^1$ can be $C_{1-6}$ alkyl or $C_{3-8}$ cycloalkyl. $R^3$ can be hydrogen or $C_{1-6}$ alkyl, or is combined with $L^1$ and the nitrogen to which they are attached to from a $C_{5-8}$ heterocycloalkyl having 1 to 2 additional heteroatoms that each can independently be N, O or S. Subscripts m and n can each independently be an integer from 1 to 4. When $R^1$ is —C(O)OH, $R^{2a}$ is Cl, CF$_3$ or —OCF$_3$, $R^3$ is hydrogen, and subscripts m and n are both 1, then $L^1$ is $C_{1-6}$ alkyl. When $R^1$ is —C(O)O$R^{1a}$ or —C(O)N($R^{1a}$)($R^{1b}$), $L^1$ is cyclohexyl, $R^{2a}$ is —OCF$_3$, $R^3$ is hydrogen, and subscripts m and n are both 1, then $R^{1a}$ is $C_{3-6}$ alkyl, $C_{1-6}$ hydroxyalkyl, or $C_{1-6}$ alkyl-$C_{6-12}$ aryl. The compounds of formula IIc can also be the pharmaceutically acceptable salts or isomers thereof.

In another embodiment, the present invention provides a method for inhibiting a soluble epoxide hydrolase and fatty acid amide hydrolase, the method including contacting the soluble epoxide hydrolase and fatty acid amide hydrolase with a therapeutically effective amount of a compound of formula II:

(II)

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. $R^2$ can be $C_{3-8}$ cycloalkyl, $C_{3-10}$ heterocycloalkyl, $C_{6-12}$ aryl, or $C_{5-12}$ heteroaryl, optionally substituted with 1 to 2 $R^{2a}$ groups. Each $R^{2a}$ can independently be hydrogen, $C_{1-6}$ alkyl, halogen, $C_{1-6}$ haloalkyl, $C_{1-6}$ alkoxy, or $C_{1-6}$ haloalkoxy. $L^1$ can be $C_{1-6}$ alkylene, $C_{3-8}$ cycloalkylene, $C_{3-10}$ heterocycloalkylene, $C_{6-12}$ arylene, or $C_{5-12}$ heteroarylene. $R^3$ can be hydrogen or $C_{1-6}$ alkyl, or is combined with $L^1$ and the nitrogen to which they are attached to form a $C_{5-8}$ heterocycloalkyl having 1 to 2 additional heteroatoms that each can independently be N, O or S. X can be CH or N. Subscript n can be an integer from 1 to 4.

In another embodiment, the present invention provides a method of treating cancer, the method including administering to a subject in need of such treatment, a therapeutically effective amount of a compound of formula II.

DETAILED DESCRIPTION OF THE INVENTION

I. General

Figure 1:
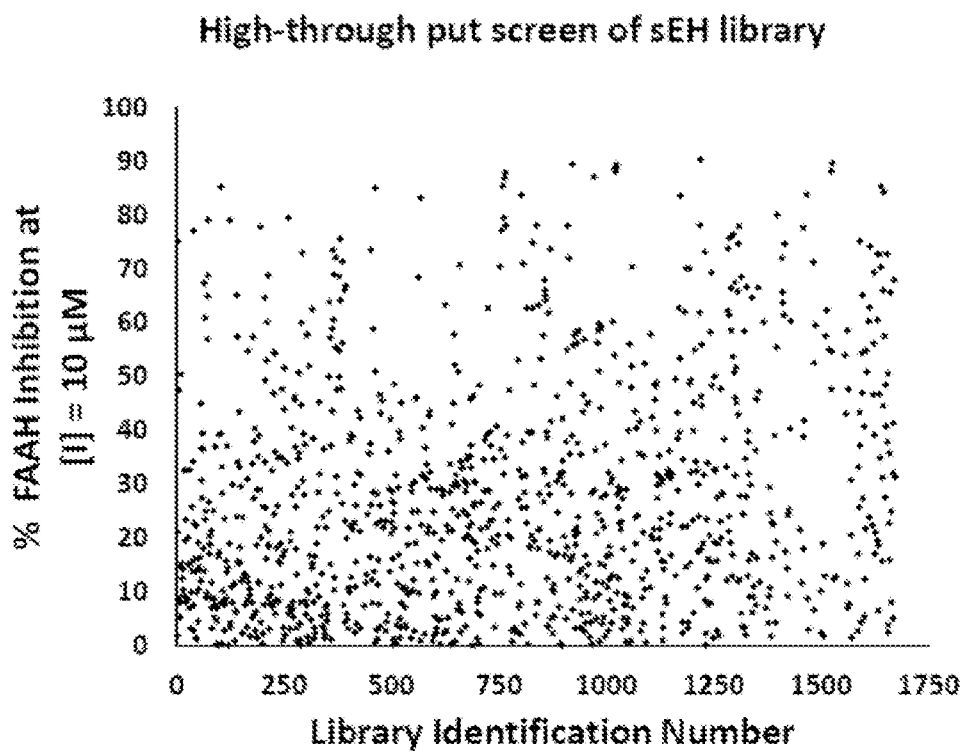
FIG. 1 shows results of a high-throughput screen of a library of inhibitors of soluble epoxide hydrolase (sEH) to identify compounds also capable of inhibiting fatty acid amide hydrolase (FAAH).

The present invention provides dual inhibitor compounds capable of inhibiting a soluble epoxide hydrolase (sEH) and fatty acid amide hydrolase (FAAH) and thereby providing beneficial therapeutic effects. The present invention also provides methods of treating diseases and disorders, such as cancer, by inhibiting an epoxide hydrolase and fatty acid amide hydrolase with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$.

Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted.

"Alkylhydroxy" or "hydroxyalkyl" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms.

As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_4$-8, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbomane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbomene, and norbomadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkylene" refers to a cycloalkyl group having the number of carbon atoms indicated, and linking at least two other groups, i.e., a divalent radical. The two moieties linked to the cycloalkylene can be linked to the same atom or different atoms of the cycloalkylene group. Examples of cycloalkylene rings include cyclopropylene, cyclobutylene, cyclopentylene and cyclohexylene, among others. Cycloalkylene groups can be linked 1,1, 1,2, 1,3, or 1,4. The cyclohexylene ring, for example, can adopt a number of conformations, including the boat and chair conformations. The chair conformation of cyclohexylene can have substituents in an axial or equatorial orientation. The divalent nature of the cycloalkylenes results in cis and trans formations where cis refers to both substituents being on the same side (top or bottom) of the cycloalkylene ring, and where trans refers to the substituents being on on opposite sides of the cycloalkylene ring. For example, cis-1,2- and cis-1,4-cyclohexylene can have one substituent in the axial orientation and the other substituent in the equatorial orientation, while trans-1,2- and trans-1,4-cyclohexylene have both substituents in the axial or equatorial orientation. cis-1,3-cyclohexylene have both substituents in the axial or equatorial orientation, and trans-1,3-cyclohexylene can have one substituent in the axial orientation and the other substituent in the equatorial orientation. Cycloalkylene groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocyclalkylene" refers to a heterocyclalkyl group, as defined above, linking at least two other groups. The two moieties linked to the heterocyclalkylene can be linked to the same atom or different atoms of the heterocyclalkylene. Heterocycloalkylene groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Arylene" refers to an aryl group, as defined above, linking at least two other groups. The two moieties linked to the aryl can be linked to the same atom or different atoms of the aryl. Arylene groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroarylene" refers to a heteroaryl group, as defined above, linking at least two other groups. The two moieties linked to the heteroaryl are linked to different atoms of the heteroaryl. Heteroarylene groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_1$-2, $C_1$-3, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

The groups defined above can optionally be substituted by any suitable number and type of substituents. Representative substituents include, but are not limited to, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O) OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$, R', R" and R'" each independently refer to hydrogen, unsubstituted alkyl, such as unsubstituted $C_{1-6}$ alkyl. Alternatively, R' and R", or R" and R'", when attached to the same nitrogen, are combined with the nitrogen to which they are attached to form a heterocycloalkyl or heteroaryl ring, as defined above.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Subject" refers to animals such as mammals, including, but not limited to, primates (e.g., humans), cows, sheep, goats, horses, dogs, cats, rabbits, rats, mice and the like. In certain embodiments, the subject is a human.

"Inhibition", "inhibits" and "inhibitor" refer to a compound that prohibits or a method of prohibiting, a specific action or function.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

III. Compounds

The present invention provides inhibitors of epoxide hydrolases and fatty acid amide hydrolases of formulas J, I and II.

Formula J

In some embodiments, the present invention provides compounds having the structure:

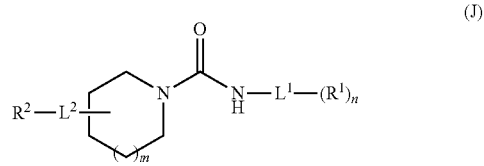

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. $L^1$ can be $C_{6-10}$ arylene or $C_{5-10}$ heteroarylene. $L^2$ is absent or $C_{1-6}$ alkylene. $R^2$ can be $C_{6-12}$ aryl or $C_{5-12}$ heteroaryl, optionally substituted with 1 to 2 $R^{2a}$ groups. Each $R^{2a}$ can independently be hydrogen, $C_{6-12}$ aryl, —O—$C_{6-12}$ aryl, $C_{5-12}$ heteroaryl or —O—$C_{5-12}$ heteroaryl, wherein the $C_{6-12}$ aryl and $C_{5-12}$ heteroaryl groups are optionally substituted with 1 to 2 $R^{2b}$ groups. Each $R^{2b}$ can independently be halogen, $C_{1-6}$ haloalkyl, $C_{1-6}$ alkoxy or $C_{1-6}$ haloalkoxy. Subscript m is 0 or 1. Subscript n is an integer from 1 to 4. When $R^2$ is quinolin-3-yl, $L^2$ is methylene, subscripts m and n are both 1, and $L^1$ is phenylene, then $R^1$ can be $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. The compounds of formula J can also be the pharmaceutically acceptable salts or isomers thereof.

In some embodiments, $L^1$ can be phenylene or $C_{5-6}$ heteroarylene. In some embodiments, $L^1$ can be phenylene or $C_{5-6}$ heteroarylene, wherein the heteroarylene comprises 1 to 2 heteroatoms each independently selected from the group consisting of N and O. In some embodiments, $L^1$ can be phenylene, pyridyl, pyridazinyl or isoxazolyl. In some embodiments, $L^1$ can be phenylene or pyridyl.

In some embodiments, the compound can be:

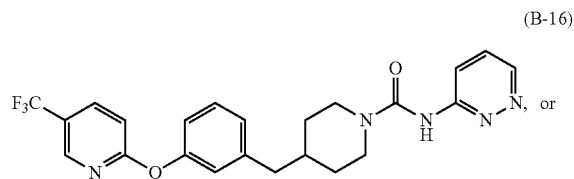

-continued (B-17)

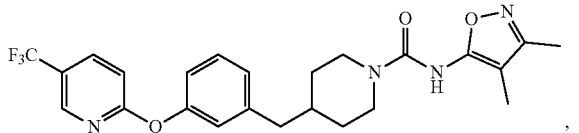

or a pharmaceutically acceptable salt or isomer thereof.

Other compounds of formula J include compounds of formula I and formula II.

Formula I

In some embodiments, the present invention provides compounds having the structure:

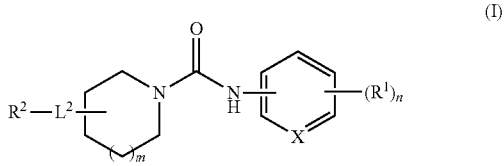

(I)

wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2$$R^{1a}$, —S(O)$_2$N($R^{1a}$)($R^{1b}$), —N($R^{1b}$)S(O)$_2$$R^{1a}$, $C_{3-8}$ cycloalkyl, $C_{5-10}$ heterocycloalkyl, $C_{6-12}$ aryl and $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. $L^2$ can be absent or $C_{1-6}$ alkylene. $R^2$ can be $C_{6-12}$ aryl or $C_{5-12}$ heteroaryl, optionally substituted with 1 to 2 $R^{2a}$ groups. Each $R^{2a}$ can independently be hydrogen, $C_{6-12}$ aryl, —O—$C_{6-12}$ aryl, $C_{5-12}$ heteroaryl or —O—$C_{5-12}$ heteroaryl, wherein the $C_{6-12}$ aryl and $C_{5-12}$ heteroaryl groups are optionally substituted with 1 to 2 $R^{2b}$ groups. Each $R^{2b}$ can independently be halogen, $C_{1-6}$ haloalkyl, $C_{1-6}$ alkoxy or $C_{1-6}$ haloalkoxy. X can be CH or N. Subscript m can be 0 or 1. Subscript n can be an integer from 1 to 4. When $R^2$ is quinolin-3-yl, $L^2$ is methylene, subscripts m and n are both 1, and X is CH, then $R^1$ can be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2$$R^{1a}$, —S(O)$_2$N($R^{1a}$)($R^{1b}$), —N($R^{1b}$)S(O)$_2$$R^{1a}$, $C_{3-8}$ cycloalkyl, $C_{5-10}$ heterocycloalkyl, $C_{6-12}$ aryl or $C_{5-12}$ heteroaryl. The compounds of formula I can also be the pharmaceutically acceptable salts or isomers thereof.

In some embodiments, each $R^1$ of formula I can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2$$R^{1a}$, —S(O)$_2$N($R^{1a}$)($R^{1b}$), —N($R^{1b}$)S(O)$_2$$R^{1a}$, $C_{3-8}$ cycloalkyl, $C_{5-10}$ heterocycloalkyl, $C_{6-12}$ aryl or $C_{5-12}$ heteroaryl. In some embodiments, each $R^1$ of formula I can independently be hydrogen, $C_{1-6}$ alkyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —C(O)N($R^{1a}$)CH$_2$C(O)O$R^{1b}$, or $C_{5-12}$ heteroaryl. In some embodiments, each $R^1$ can be $C_{1-6}$ alkyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —C(O)N($R^{1a}$)CH$_2$C(O)O$R^{1b}$, or $C_{5-12}$ heteroaryl. In some embodiments, each $R^1$ can be hydrogen, $C_{1-6}$ alkyl, hydroxy, $C_{1-6}$ hydroxyalkyl, halogen, $C_{1-6}$ haloalkyl, $C_{1-6}$ alkoxy, or $C_{1-6}$ haloalkoxy. In some embodiments, $R^1$ can be —CN, —C(O)$R^{1a}$, —C(O)O$R^{1a}$, —OC(O)$R^{1a}$, —C(O)N($R^{1a}$)($R^{1b}$), —C(O)N($R^{1a}$)CH$_2$C(O)O$R^{1b}$, or $C_{5-12}$ heteroaryl. In some embodiments, $R^1$ can be hydrogen, halogen, $C_{1-6}$ alkoxy, or $C_{1-6}$ haloalkoxy. In some embodiments, $R^1$ can be halogen or $C_{1-6}$ alkoxy. In some embodiments, $R^1$ can be hydrogen, fluoro, chloro, —OCF$_3$, or —OCH$_3$. In some embodiments, $R^1$ can be hydrogen.

In some embodiments, $R^1$ of formula I can be —C(O)$R^{1a}$, —C(O)O$R^{1a}$, —OC(O)$R^{1a}$, —C(O)N($R^{1a}$)($R^{1b}$), or —C(O)N($R^{1a}$)CH$_2$C(O)O$R^{1b}$. In some embodiments, $R^{1a}$ can be hydrogen, $C_{1-6}$ alkyl, $C_{1-6}$ hydroxyalkyl, or $C_{1-6}$ alkyl-$C_{6-12}$ aryl. In some embodiments, $R^{1b}$ can be hydrogen or $C_{1-6}$ alkyl. The alkyl of $R^{1a}$ or $R^{1b}$ can independently be any suitable alkyl group, such as methyl, ethyl, propyl, butyl, pentyl, and hexyl, among others.

In some embodiments, $L^2$ of formula I can be absent or $C_{1-6}$ alkylene. In some embodiments, $L^2$ can be absent or $C_{1-4}$ alkylene. In some embodiments, $L^2$ can absent or methylene. In some embodiments, $L^2$ is absent. In some embodiments, $L^2$ is methylene.

In some embodiments, $R^2$ of formula I can be $C_{6-12}$ aryl or $C_{5-12}$ heteroaryl, optionally substituted with 1 to 2 $R^{2a}$ groups. In some embodiments, $R^2$ is $C_{5-12}$ heteroaryl, optionally substituted with 1 to 2 $R^{2a}$ groups. In some embodiments, $R^2$ can be phenyl, naphthyl, pyridyl, quinolinyl, thiazolyl, imidazolyl, or triazolyl, each of which is optionally substituted with 1 $R^{2a}$ group. In some embodiments, $R^2$ can be naphthyl or quinolinyl, each of which is optionally substituted with 1 $R^{2a}$ group. In some embodiments, $R^2$ is quinolin-3-yl. In some embodiments, $R^2$ can be phenyl or thiazolyl, each of which is optionally substituted with 1 $R^{2a}$ group.

In some embodiments, each $R^{2a}$ of formula I can independently be hydrogen, $C_{6-12}$ aryl, —O—$C_{6-12}$ aryl, $C_{5-12}$ heteroaryl and —O—$C_{5-12}$ heteroaryl, wherein the $C_{6-12}$ aryl and $C_{5-12}$ heteroaryl groups are optionally substituted with 1 to 2 $R^{2b}$ groups. In some embodiments, each $R^{2a}$ of formula I can be hydrogen, $C_{6-12}$ aryl, —O—$C_{6-12}$ aryl, and $C_{5-12}$ heteroaryl, wherein the $C_{6-12}$ aryl and $C_{5-12}$ heteroaryl groups are optionally substituted with 1 $R^{2b}$ group. In some embodiments, $R^{2a}$ is hydrogen. In some embodiments, $R^{2a}$ can be phenyl or pyridyl, each of which is optionally substituted with 1 $C_{1-6}$ haloalkyl group.

In some embodiments, each $R^{2b}$ of formula I can independently be halogen, $C_{1-6}$ haloalkyl, $C_{1-6}$ alkoxy or $C_{1-6}$ haloalkoxy. In some embodiments, each $R^{2b}$ is $C_{1-6}$ haloalkyl. In some embodiments, each $R^{2b}$ is $C_1$-haloalkyl. In some embodiments, each $R^{2b}$ is —CF$_3$.

In some embodiments, X of formula I is CH or N. In some embodiments, X is CH$_3$. In some embodiments, X is N. In some embodiments, subscripts m of formula I can be 0 or 1. In some embodiments, subscript m is 0. In some embodiments, subscript m is 1. In some embodiments, subscript n of formula I can be an integer from 1 to 4. In some embodiments, subscript n is 1.

In some embodiments, the compounds of formula I have the following structure:

(Ia)

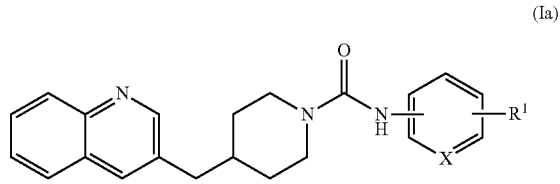

wherein X can be CH or N; and R¹ can be hydrogen, $C_{1-6}$ alkyl, hydroxy, $C_{1-6}$ hydroxyalkyl, halogen, $C_{1-6}$ haloalkyl, $C_{1-6}$ alkoxy, or $C_{1-6}$ haloalkoxy. In some embodiments, X is CH. In some embodiments, X is N. In some embodiments, R¹ can be hydrogen, halogen, or $C_{1-6}$ alkoxy. In some embodiments, R¹ can be halogen or $C_{1-6}$ alkoxy. In some embodiments, R¹ is hydrogen. In some embodiments, X is CH and R¹ can be halogen or $C_{1-6}$ alkoxy. In some embodiments, X is N and R¹ is hydrogen.

In some embodiments, the compound of formula I can be:

(B-1)

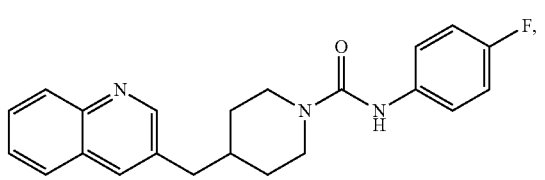

(B-2)

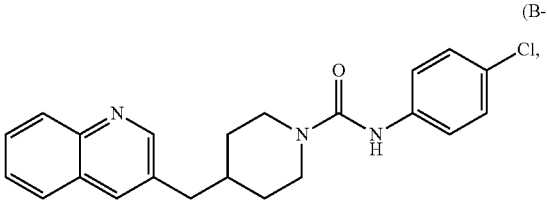

(B-3)

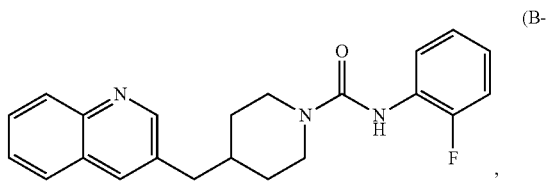

(B-4)

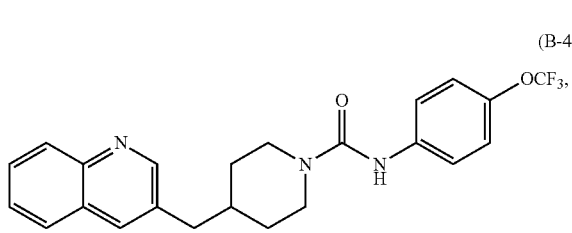

(B-5)

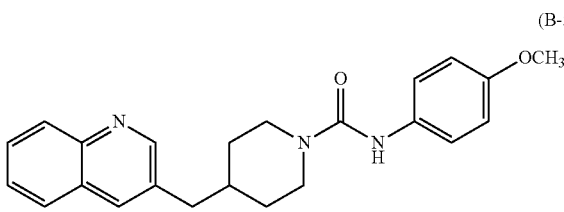

(B-6)

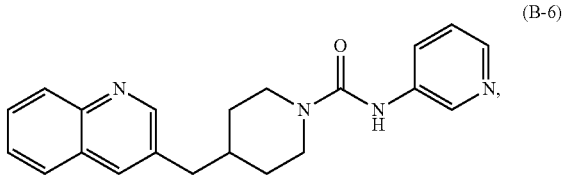

or a pharmaceutically acceptable salt or isomer thereof.

In some embodiments, the compounds of formula I have the following structure:

(Ib)

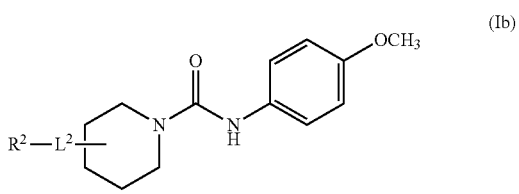

wherein $L^2$, $R^2$, $R^{2a}$, and $R^{2b}$ are as defined above.

In some embodiments, the compound of formula I can be:

(B-7)

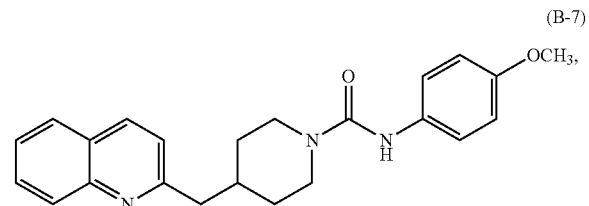

(B-8)

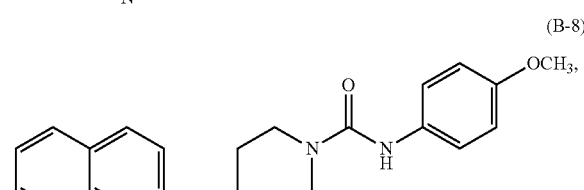

(B-9)

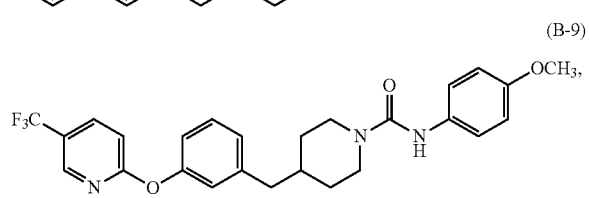

(B-10)

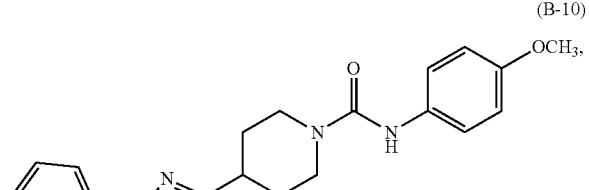

or a pharmaceutically acceptable salt or isomer thereof.

In some embodiments, the compound of formula I can a compound of formula Ic:

(Ic)

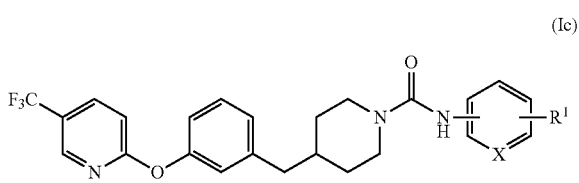

wherein R¹ can be hydrogen, $C_{1-6}$ alkyl, hydroxy, $C_{1-6}$ hydroxyalkyl, halogen, $C_{1-6}$ haloalkyl, $C_{1-6}$ alkoxy, or $C_{1-6}$ haloalkoxy. In some embodiments, the compound of formula Ic can be:

(B-9)

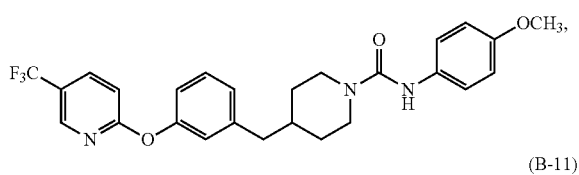

(B-11)

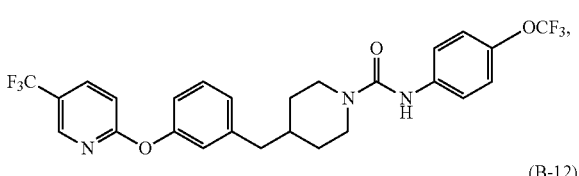

(B-12)

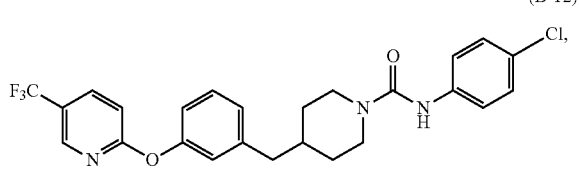

(B-13)

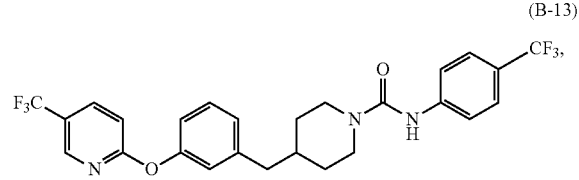

(B-14)

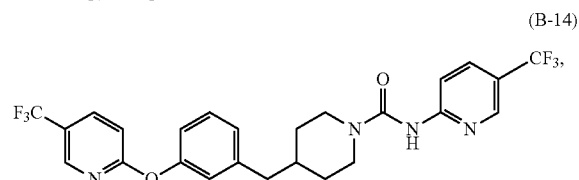

(B-15)

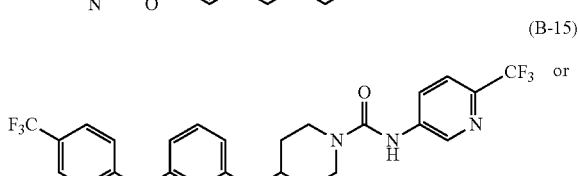

(B-18)

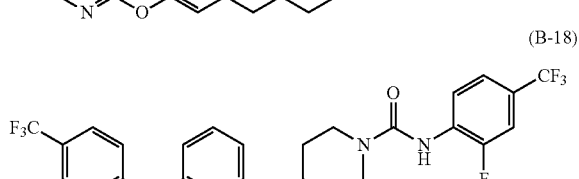

or a pharmaceutically acceptable salt or isomer thereof.

Formula II

In some embodiments, the present invention provides a compound having the formula:

(II)

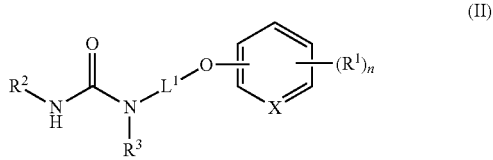

wherein R¹ can be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)R$^{1a}$, —C(O)OR$^{1a}$, —OC(O)R$^{1a}$, —C(O)N(R$^{1a}$)(R$^{1b}$), —N(R$^{1b}$)C(O)R$^{1a}$, —C(O)N(R$^{1a}$)CH$_2$C(O)OR$^{1b}$, —N(R$^{1a}$)(R$^{1b}$), —S(O)$_2$R$^{1a}$, —S(O)$_2$N(R$^{1a}$)(R$^{1b}$), —N(R$^{1b}$)S(O)$_2$R$^{1a}$, $C_{3-8}$ cycloalkyl, $C_{5-10}$ heterocycloalkyl, $C_{6-12}$ aryl or $C_{5-12}$ heteroaryl. R$^{1a}$ can be hydrogen, $C_{1-6}$ alkyl, $C_{1-6}$ hydroxyalkyl, or $C_{1-6}$ alkyl-$C_{6-12}$ aryl. R$^{1b}$ can be hydrogen or $C_{1-6}$ alkyl. R² can be $C_{3-8}$ cycloalkyl, $C_{3-10}$ heterocycloalkyl, $C_{6-12}$ aryl, or $C_{5-12}$ heteroaryl, optionally substituted with 1 to 2 R$^{2a}$ groups. Each R$^{2a}$ can independently be hydrogen, $C_{1-6}$ alkyl, halogen, $C_{1-6}$ haloalkyl, $C_{1-6}$ alkoxy, or $C_{1-6}$ haloalkoxy. L¹ can be $C_{1-6}$ alkylene, $C_{3-8}$ cycloalkylene, $C_{3-10}$ heterocycloalkylene, $C_{6-12}$ arylene, or $C_{5-12}$ heteroarylene. R³ can be hydrogen or $C_{1-6}$ alkyl, or can be combined with L¹ and the nitrogen to which they are attached to form a $C_{5-8}$ heterocycloalkyl having 1 to 2 additional heteroatoms each independently selected from N, O and S. X can be CH or N. Subscript n is an integer from 1 to 4.

In some embodiments, the compounds of formula II can be:

(A-1)

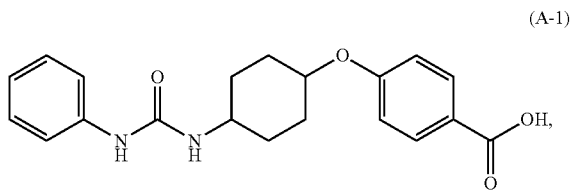

(A-2)

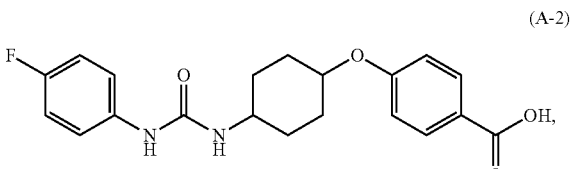

(A-6)

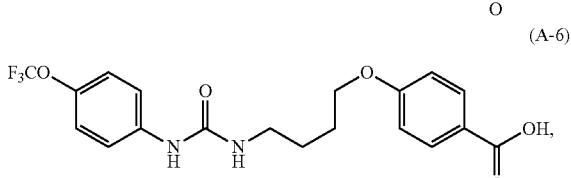

(A-7)

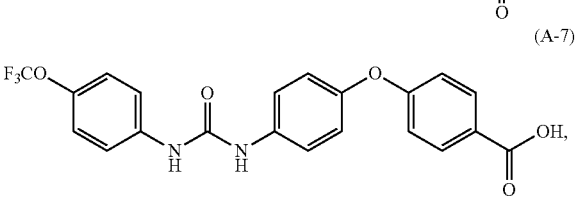

or a pharmaceutically acceptable salt or isomer thereof.

In some embodiments, the compounds of formula II have the following structure:

(IIa)

wherein $R^{2a}$ is as defined above for formula II.

In some embodiments, the compound of formula IIa can be:

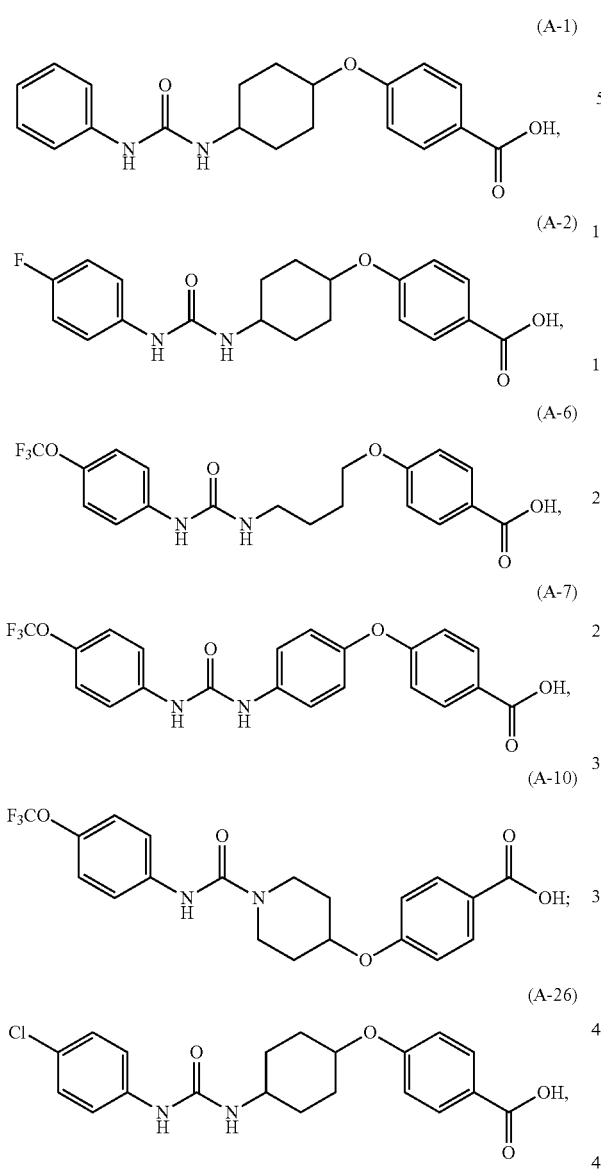
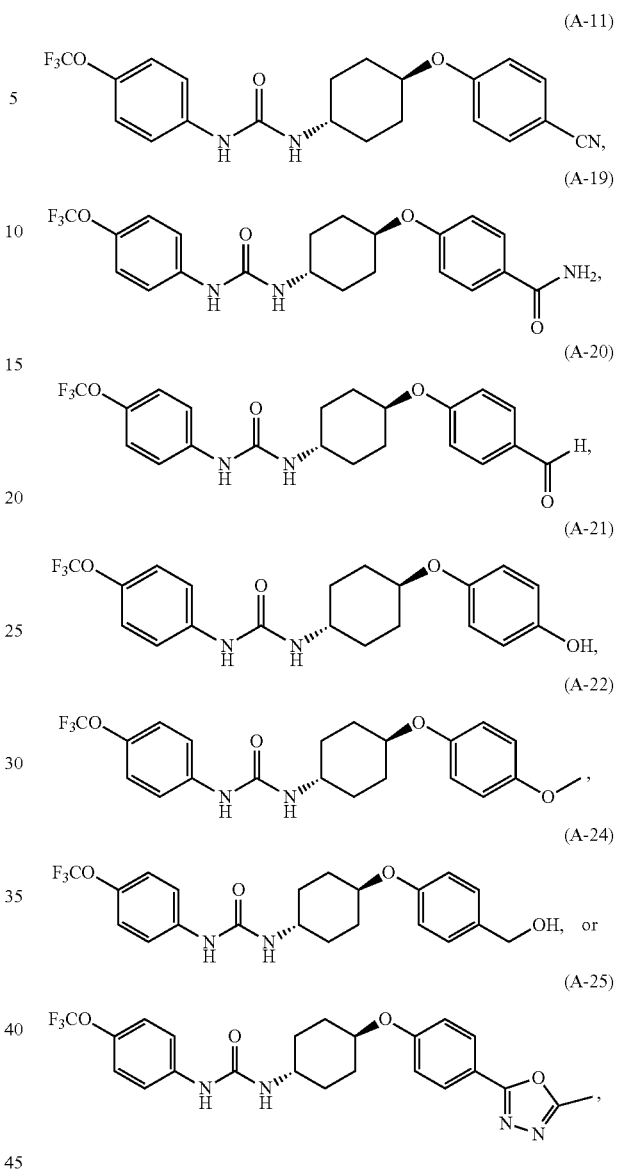

or a pharmaceutically acceptable salt or isomer thereof.

In some embodiments, the compounds of formula II have the following structure:

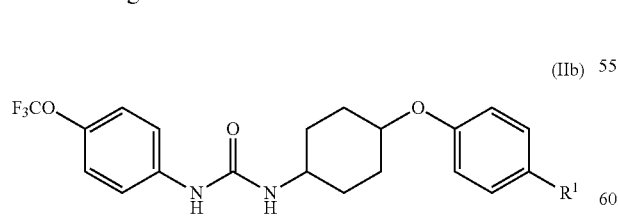

wherein $R^1$ is as defined above for formula II.

In some embodiments, the compound of formula IIb can be:

or a pharmaceutically acceptable salt or isomer thereof.

In some embodiments, the present invention provides compounds having the structure:

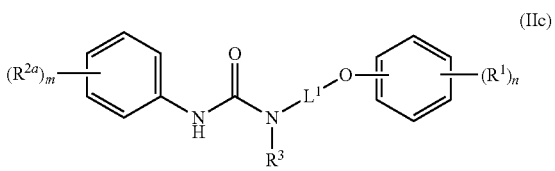

wherein each $R^1$ can independently be hydrogen, hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl. $R^{1a}$ can be hydrogen, $C_{1-6}$ alkyl, $C_{1-6}$ hydroxyalkyl, or $C_{1-6}$ alkyl-$C_{6-12}$ aryl. $R^{1b}$ can be hydrogen or $C_{1-6}$ alkyl. Each $R^{2a}$ can independently be hydrogen, $C_{1-6}$ alkyl, halogen, $C_{1-6}$ haloalkyl, $C_{1-6}$ alkoxy or $C_{1-6}$ haloalkoxy. $L^1$ can be $C_{1-6}$ alkylene or $C_{3-8}$ cycloalkylene. $R^3$ can be hydrogen or $C_{1-6}$ alkyl, or is combined with $L^1$ and the nitrogen to which they are attached to from a $C_{5-8}$ heterocycloalkyl having 1 to 2 additional heteroatoms that each can independently be N, O or S. Subscripts m and n can each independently be an integer from 1 to 4. When $R^1$ is —C(O)OH, $R^{2a}$ is Cl, $CF_3$ or —$OCF_3$, $R^3$ is hydrogen, and subscripts m and n are both 1, then $L^1$ is $C_{1-6}$ alkylene. When $R^1$ is —$C(O)OR^{1a}$ or —$C(O)N(R^{1a})(R^{1b})$, $L^1$ is cyclohexylene, $R^{2a}$ is —$OCF_3$, $R^3$ is hydrogen, and subscripts m and n are both 1, then $R^{1a}$ can be $C_{3-6}$ alkyl, $C_{1-6}$ hydroxyalkyl, or $C_{1-6}$ alkyl-$C_{6-12}$ aryl. The compounds of formula IIc can also be the pharmaceutically acceptable salts or isomers thereof.

In some embodiments, each $R^1$ of formula IIc can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —$C(O)R^{1a}$, —$C(O)OR^{1a}$, —$OC(O)R^{1a}$, —$C(O)N(R^{1a})(R^{1b})$, —$N(R^{1b})C(O)R^{1a}$, —$C(O)N(R^{1a})CH_2C(O)OR^{1b}$, —$N(R^{1a})(R^{1b})$, —$S(O)_2R^{1a}$, —$S(O)_2N(R^{1a})(R^{1b})$, —$N(R^{1b})S(O)_2R^{1a}$, $C_{3-8}$ cycloalkyl, $C_{5-10}$ heterocycloalkyl, $C_{6-12}$ aryl or $C_{5-12}$ heteroaryl. In some embodiments, each $R^1$ of formula IIc can independently be hydrogen, $C_{1-6}$ alkyl, hydroxy, $C_{1-6}$ hydroxyalkyl, $C_{1-6}$ alkoxy, —$C(O)R^{1a}$, —$C(O)OR^{1a}$, —$OC(O)R^{1a}$, —$C(O)N(R^{1a})(R^{1b})$, or $C_{5-12}$ heteroaryl. In some embodiments, each $R^1$ of formula IIc can independently be hydroxy, $C_{1-6}$ hydroxyalkyl, $C_{1-6}$ alkoxy, —$C(O)R^{1a}$, —$C(O)OR^{1a}$, —$OC(O)R^{1a}$, —$C(O)N(R^{1a})(R^{1b})$, or $C_{5-12}$ heteroaryl. In some embodiments, each $R^1$ can independently be —$C(O)OR^{1a}$ or —$C(O)N(R^{1a})(R^{1b})$. In some embodiments, each $R^1$ can be —C(O)OH, —C(O)H, hydroxy, —$CH_2OH$, —$OCH_3$, or oxadiazolyl. In some embodiments, each $R^1$ can be —C(O)OH.

In some embodiments, each $R^1$ of formula IIc can independently —$C(O)R^{1a}$, —$C(O)OR^{1a}$, —$OC(O)R^{1a}$, or —$C(O)N(R^a)(R^{1b})$. In some embodiments, $R^{1a}$ of formula IIc can be hydrogen, $C_{1-6}$ alkyl, $C_{1-6}$ hydroxyalkyl, or $C_{1-6}$ alkyl-$C_{6-12}$ aryl. In some embodiments, $R^{1a}$ can be $C_{3-6}$ alkyl, $C_{1-6}$ hydroxyalkyl, or $C_{1-6}$ alkyl-$C_{6-12}$ aryl. In some embodiments, $R^{1a}$ can be isopropyl, benzyl, or hydroxyethyl. In some embodiments, $R^{1a}$ is hydrogen. In some embodiments, $R^{1b}$ of formula IIc can be hydrogen or $C_{1-6}$ alkyl. In some embodiments, $R^{1b}$ is hydrogen. In some embodiments, $R^{1b}$ can be $C_{1-6}$ alkyl. The alkyl of $R^{1a}$ or $R^{1b}$ can independently be any suitable alkyl group, such as methyl, ethyl, propyl, butyl, pentyl, and hexyl, among others.

In some embodiments, each $R^{2a}$ of formula IIc can independently be hydrogen, $C_{1-6}$ alkyl, halogen, $C_{1-6}$ haloalkyl, $C_{1-6}$ alkoxy or $C_{1-6}$ haloalkoxy. In some embodiments, each $R^{2a}$ can independently be hydrogen, fluoro, or —$OCF_3$ In some embodiments, each $R^{2a}$ can be —$OCF_3$.

In some embodiments, $L^1$ of formula IIc can be $C_{1-6}$ alkylene or $C_{3-8}$ cycloalkylene. In some embodiments, $L^1$ can be n-butylene or cyclohexylene. In some embodiments, $L^1$ can be 1,4-cyclohexylene. In some embodiments, $L^1$ can be cis-1,4-cyclohexylene. In some embodiments, $L^1$ can be trans-1,4-cyclohexylene.

In some embodiments, $R^3$ of formula IIc can be hydrogen or $C_{1-6}$ alkyl. In some embodiments, $R^3$ is hydrogen. In some embodiments, $R^3$ is combined with $L^1$ and the nitrogen to which they are attached to form a $C_{5-8}$ heterocycloalkyl having 1 to 2 additional heteroatoms each independently selected from N, O and S. In some embodiments, $R^3$ is combined with $L^1$ and the nitrogen to which they are attached to form a divalent piperidinyl group.

In some embodiments, subscript m is an integer from 1 to 4. In some embodiments, m is 1. In some embodiments, subscript n is an integer from 1 to 4. In some embodiments, n is 1. In some embodiments, both m and n are 1.

In some embodiments, the compound of formula IIc can be:

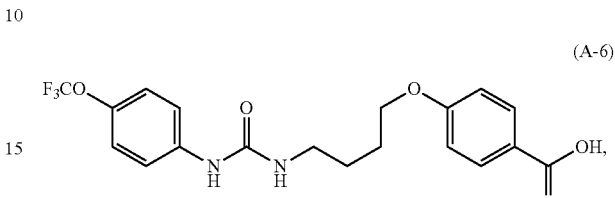

(A-6)

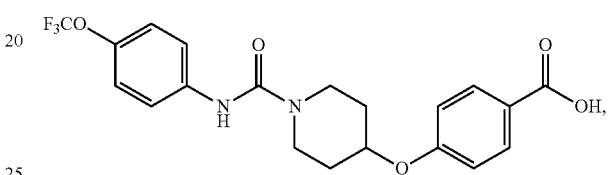

(A-10)

or a pharmaceutically acceptable salt or isomer thereof.

In some embodiments, the compounds of formula IIc have the following structure:

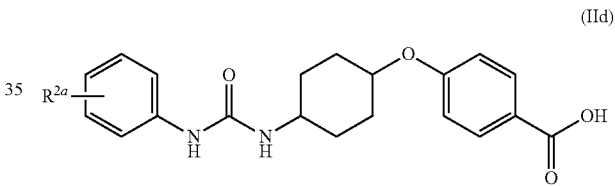

(IId)

wherein $R^{2a}$ is as defined above for formula IIc. In some embodiments, the compound can have the structure of formula IId, wherein $R^{2a}$ can be hydrogen, $C_{1-6}$ alkyl, F, Br, $C_{2-6}$ haloalkyl, $C_{1-6}$ alkoxy or $C_{2-6}$ haloalkoxy, or a pharmaceutically acceptable salt or isomer thereof.

In some embodiments, the compound of formula IId can be:

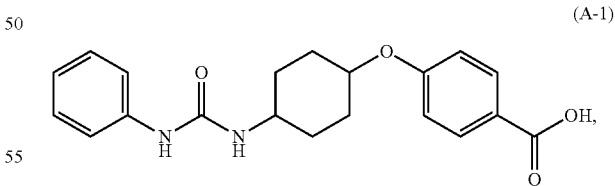

(A-1)

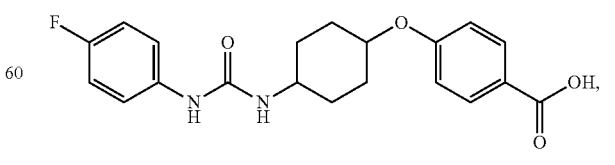

(A-2)

or a pharmaceutically acceptable salt or isomer thereof.

In some embodiments, the compounds of formula IIc have the following structure:

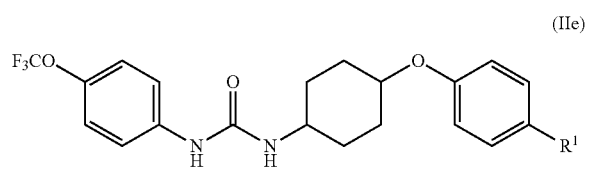

(IIe)

wherein $R^1$ is as defined above for formula IIc. In some embodiments, the compound can have the structure of formula IIe wherein each $R^1$ can independently be hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)$R^{1a}$, —C(O)O$R^{1a}$, —OC(O)$R^{1a}$, —C(O)N($R^{1a}$)($R^{1b}$), —N($R^{1b}$)C(O)$R^{1a}$, —C(O)N($R^{1a}$)CH$_2$C(O)O$R^{1b}$, —N($R^{1a}$)($R^{1b}$), —S(O)$_2R^{1a}$, —S(O)$_2$N($R^{1a}$)($R^{1b}$), —N($R^{1b}$)S(O)$_2R^{1a}$, $C_{3-8}$ cycloalkyl, $C_{5-10}$ heterocycloalkyl, $C_{6-12}$ aryl or $C_{5-12}$ heteroaryl; $R^{1a}$ can be hydrogen, $C_{1-6}$ alkyl, $C_{1-6}$ hydroxyalkyl, or $C_{1-6}$ alkyl-$C_{6-12}$ aryl; $R^{1b}$ can be hydrogen and $C_{1-6}$ alkyl; such that when $R^1$ is —C(O)O$R^{1a}$ or —C(O)N($R^{1a}$)($R^{1b}$), $L^1$ is cyclohexylene, $R^{2a}$ is —OCF$_3$, $R^3$ is hydrogen, and subscripts m and n are both 1, then $R^{1a}$ can be $C_{3-6}$ alkyl, $C_{1-6}$ hydroxyalkyl, or $C_{1-6}$ alkyl-$C_{6-12}$ aryl; or a pharmaceutically acceptable salt or isomer thereof.

In some embodiments, the compound of formula IIe can be:

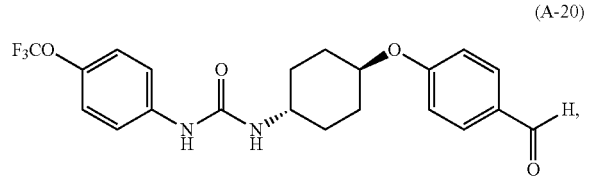
(A-20)

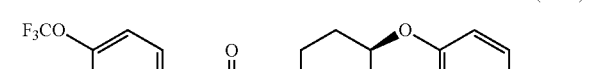
(A-21)

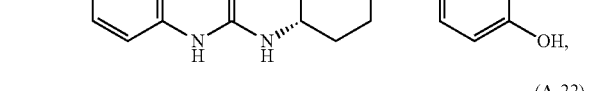
(A-22)

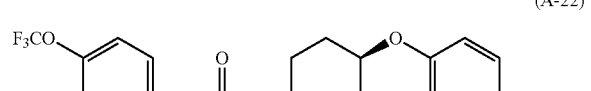
(A-24)

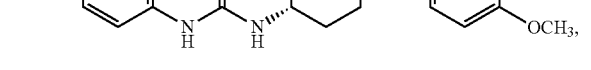
(A-25)

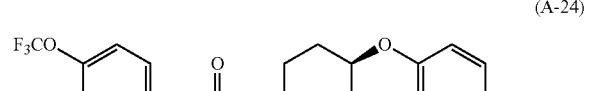

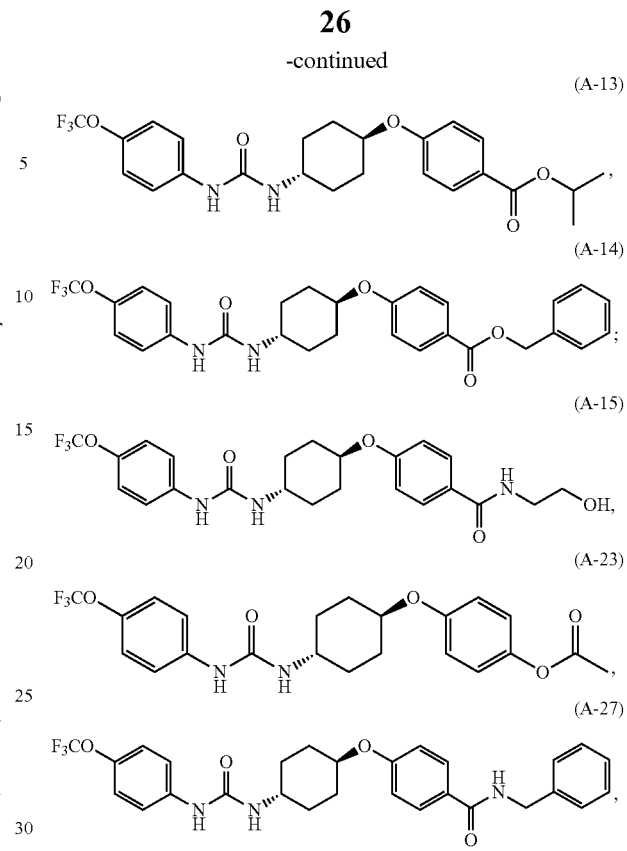

or a pharmaceutically acceptable salt or isomer thereof.

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2H$), tritium ($^3H$), iodine-125 ($^{125}I$), carbon-13 ($^{13}C$), or carbon-14 ($^{14}C$). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds described may indicate relative stereochemistry, the compounds may exist as a racemic mixture or as either enantiomer.

The methods of making the compounds of the present invention can include any suitable protecting group or protecting group strategy. A protecting group refers to a compound that renders a functional group unreactive to a particular set of reaction conditions, but that is then removable in a later synthetic step so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety.

IV. Formulations

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

In some embodiments, the formulations of the compositions of the present invention comprise solubility aids. The solubility aid can be, for example, a cyclodextrin. The use of cyclodextrins as solubility aids for highly water-insoluble steroids is discussed in U.S. Patent Application Publication Nos. US 2015/0018327 and US 2015/0313915. The cyclodextrin can be, for example, a β-cyclodextrin. In some embodiments, the cyclodextrin is a sulfo butyl ether β-cyclodextrin.

V. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order.

Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VI. Methods of Treating a Disorder

In some embodiments, the present invention provides a method of inhibiting a soluble epoxide hydrolase and fatty acid amide hydrolase, the method including contacting the soluble epoxide hydrolase and fatty acid amide hydrolase with a therapeutically effective amount of a compound of the present invention, thereby inhibiting the soluble epoxide hydrolase and fatty acid amide hydrolase. Fatty acid amide hydrolase (FAAH) and soluble epoxide hydrolase (sEH) are enzymes responsible for the regulation of physiologic homeostasis of pain, hypertension and inflammation. Both act through their respective lipid mediators to terminate analgesic compounds, thus their inhibition has been used to reduce experimental inflammatory and neuropathic pain.

In some embodiments, the soluble epoxide hydrolase and fatty acid amide hydrolase are contacted with a therapeutically effective amount of a compound having formula J. In some embodiments, the soluble epoxide hydrolase and fatty acid amide hydrolase are contacted with a therapeutically effective amount of a compound that is:

(B-16)

(B-17)

or a pharmaceutically acceptable salt or isomer thereof.

In some embodiments, the soluble epoxide hydrolase and fatty acid amide hydrolase are contacted with a therapeutically effective amount of a compound having formula I. In some embodiments, the soluble epoxide hydrolase and fatty acid amide hydrolase are contacted with a therapeutically effective amount of a compound that is:

(B-1)

(B-2)

(B-3)

(B-4)

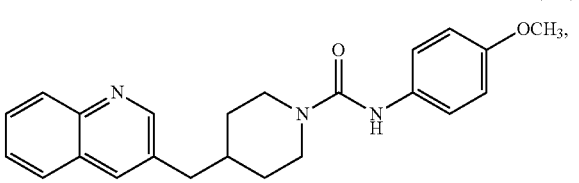
(B-5)

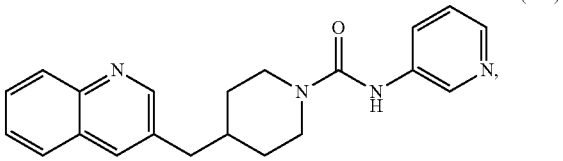
(B-6)

(B-7)

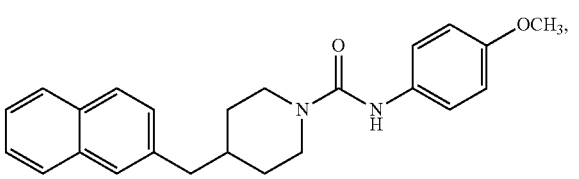
(B-8)

(B-9)

(B-10)

or a pharmaceutically acceptable salt or isomer thereof. In some embodiments, the soluble epoxide hydrolase and fatty acid amide hydrolase are contacted with a therapeutically effective amount of a compound that is:

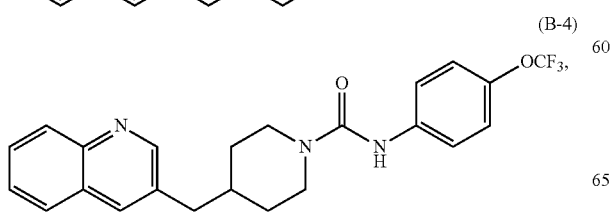
(B-9)

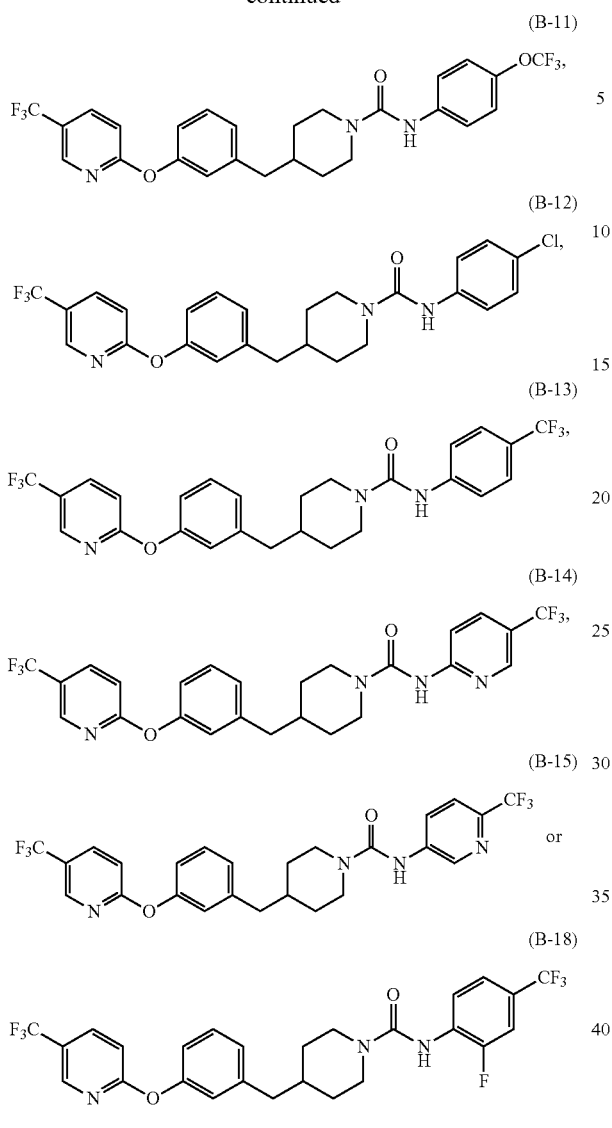

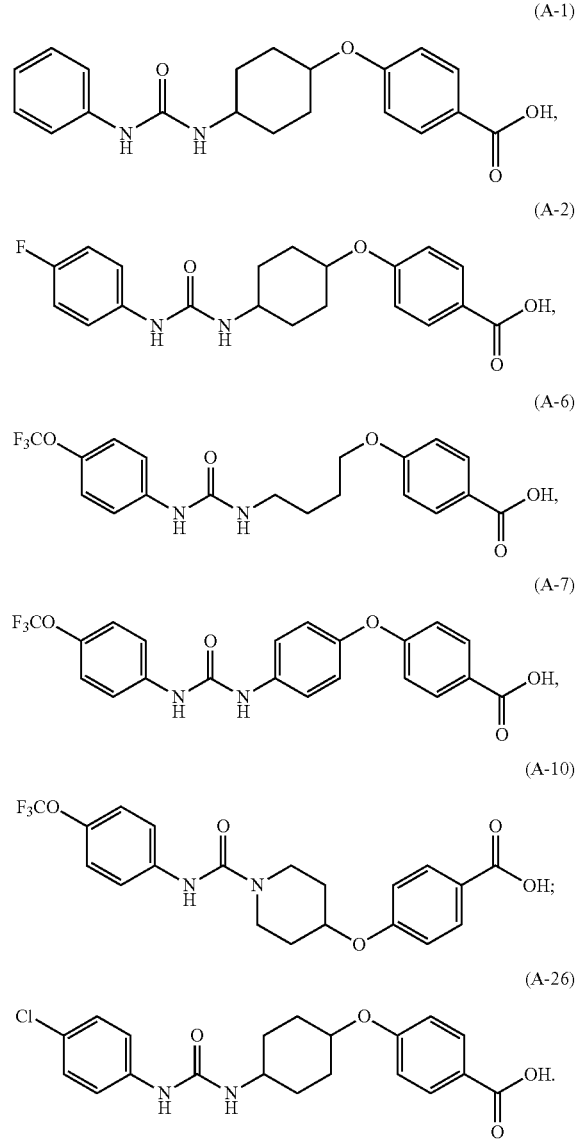

or a pharmaceutically acceptable salt or isomer thereof.

In some embodiments, the present invention provides a method for inhibiting a soluble epoxide hydrolase and fatty acid amide hydrolase, comprising contacting the soluble epoxide hydrolase and fatty acid amide hyrolase with a therapeutically effective amount of a compound of formula II, or a pharmaceutically acceptable salt or isomer thereof, thereby inhibiting the soluble epoxide hydrolase and fatty acid amide hydrolase. The compounds can be any suitable compound of formula II. For example, the compound can be a compound of formula IIa, IIb, IIc, IId or IIe. In some embodiment, the compound has a structure according to formula IIa. In some embodiment, the compound has a structure according to formula IIb. In some embodiment, the compound has a structure according to formula IIc. In some embodiment, the compound has a structure according to formula IId. In some embodiment, the compound has a structure according to formula IIe.

In some embodiments, the soluble epoxide hydrolase and fatty acid amide hydrolase are contacted with a therapeutically effective amount of a compound that is:

In some embodiments, the soluble epoxide hydrolase and fatty acid amide hydrolase are contacted with a therapeutically effective amount of a compound that is:

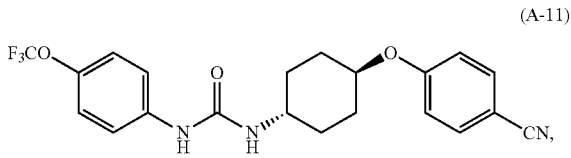

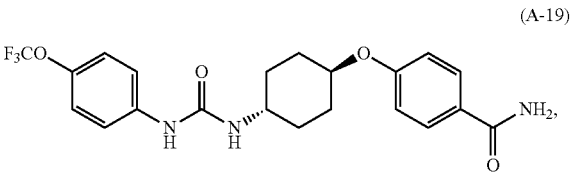

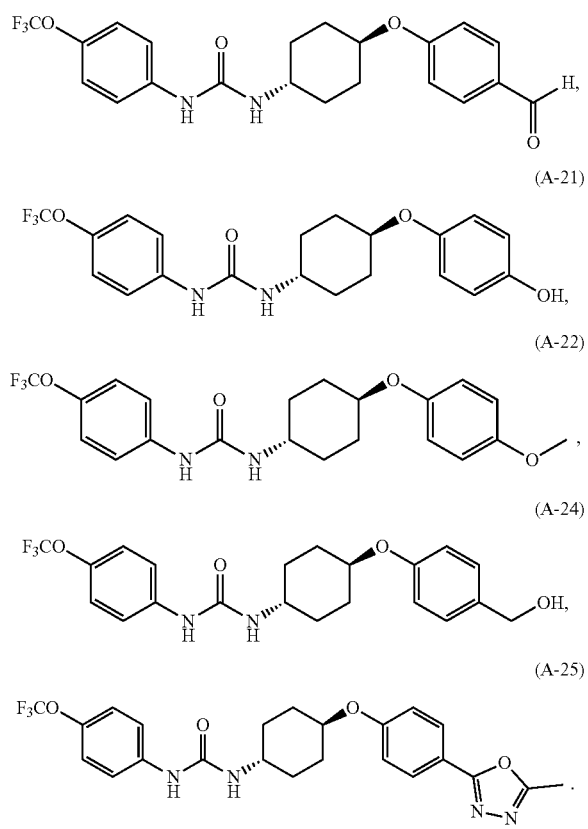

In some embodiments, the soluble epoxide hydrolase and fatty acid amide hydrolase are contacted with a therapeutically effective amount of a compound that is:

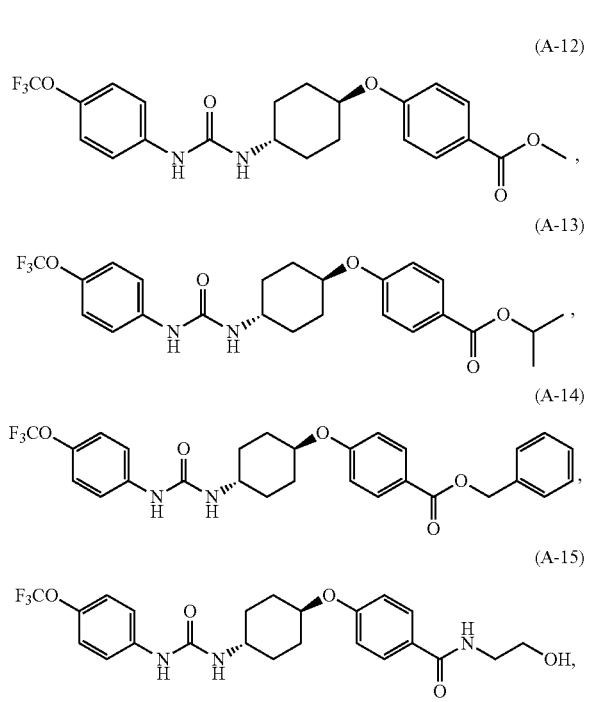

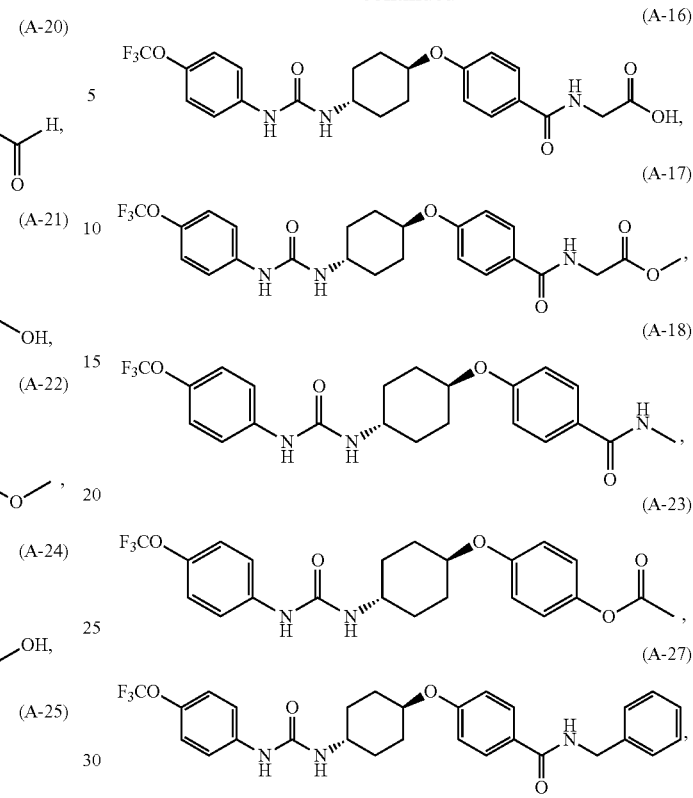

or a pharmaceutically acceptable salt or isomer thereof.

In some embodiments, the present invention provides a method of treating cancer, the method including administering to a subject in need thereof, a therapeutically effective amount of a compound of the present invention, thereby treating cancer. In some embodiments, a compound of the present invention is a chemotherapeutic agent. A chemotherapeutic agent, as used herein, refers to any compound or pharmaceutical composition useful for treating or ameliorating cancer. The agent can be given with a curative intent, with an aim to prolong life, or for the purpose of reducing symptoms.

Examples of disorders or conditions suitable for use with the present invention include, but are not limited to, acute lymphoblastic leukemia, acute myeloid leukemia, adrenocortical carcinoma, anal cancer, appendix cancer, astrocytoma, basal-cell carcinoma, bile duct cancer, bladder cancer, bone tumor, brainstem glioma, brain cancer, cerebellar astrocytoma, cerebral astrocytoma, ependymoma, medulloblastoma, supratentorial primitive neuroectodermal tumors, visual pathway and hypothalamic glioma, breast cancer, bronchial adenomas, Burkitt's lymphoma, central nervous system lymphoma, cerebellar astrocytoma, cervical cancer, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, epitheliod hemangioendothelioma (EHE), esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor (GIST), germ cell tumor, gestational trophoblastic tumor, gastric carcinoid, hairy cell leukemia, head and neck cancer, heart cancer, hepatocellular cancer, Hodgkin lymphoma, hypopharyngeal cancer, hypothalamic and visual pathway glioma, childhood, intraocular melanoma, islet cell carcinoma, Kaposi sarcoma, kidney cancer, laryngeal cancer, leukaemias, lip and oral cavity cancer, liposarcoma, liver cancer, non-small cell lung cancer, small-cell lung cancer, lymphomas, macroglobulinemia, male breast cancer, malignant fibrous histiocytoma of bone, medulloblastoma, melanoma, Merkel cell cancer, mesothelioma, metastatic squamous neck cancer, mouth cancer, multiple endocrine neoplasia syndrome, multiple myeloma, mycosis fungoides, myelodysplastic syndromes, myelogenous leukemia, myeloid leukemia, adult acute, myeloproliferative disorders, chronic, myxoma, nasal cavity and paranasal sinus cancer, nasopharyngeal carcinoma, neuroblastoma, non-Hodgkin lymphoma, oligodendroglioma, oral cancer, oropharyngeal cancer, osteosarcoma, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma, supratentorial primitive neuroectodermal tumors, pituitary adenoma. plasma cell neoplasia, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sdzary syndrome, non-melanoma skin cancer, melanoma Merkel cell skin carcinoma, small intestine cancer, squamous cell carcinoma, squamous neck cancer, stomach cancer, cutaneous T-Cell lymphoma, testicular cancer, throat cancer, thymoma, thyroid cancer, transitional cell cancer of the renal pelvis and ureter, trophoblastic tumor, gestational, urethral cancer, uterine cancer, vaginal cancer, vulvar cancer, Waldenstrom macroglobulinemia, and Wilms tumor.

In some embodiments, a subject in need of cancer treatment is administered a therapeutically effective amount of a compound of formula I. In some embodiments, a subject in need of cancer treatment is administered a therapeutically effective amount of a compound that is:

(B-1)
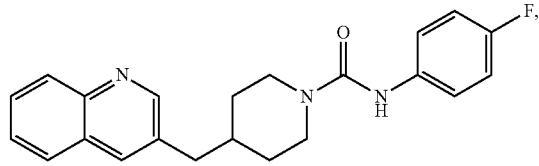

(B-2)
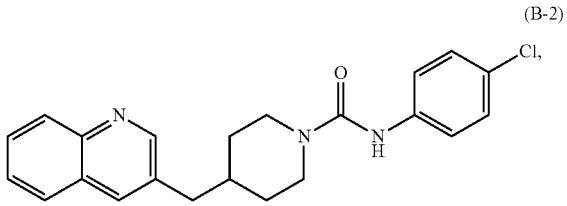

(B-3)
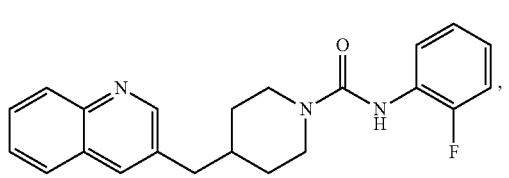

(B-4)
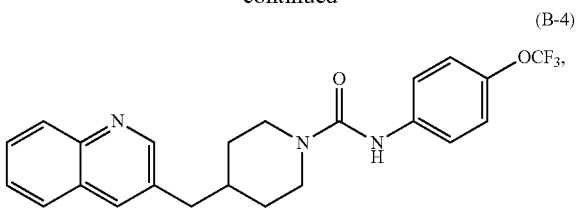

(B-5)
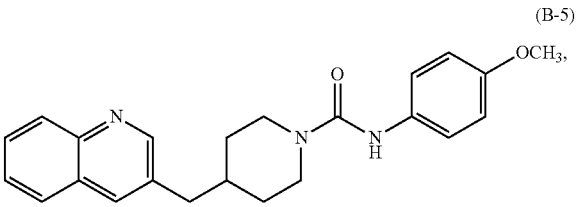

(B-6)
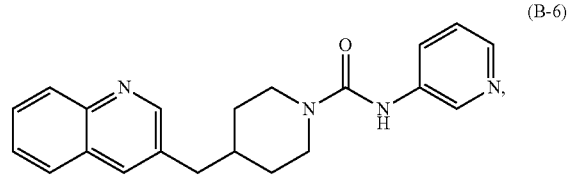

(B-7)
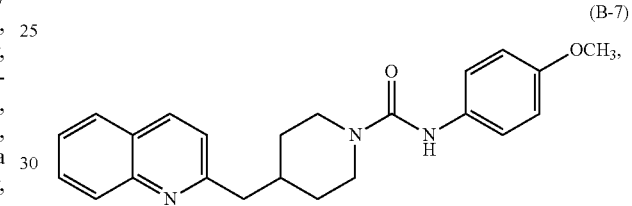

(B-8)
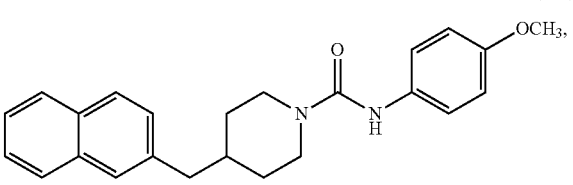

(B-9)
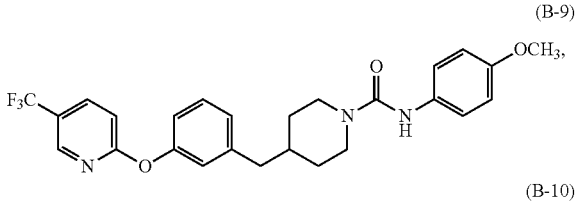

(B-10)
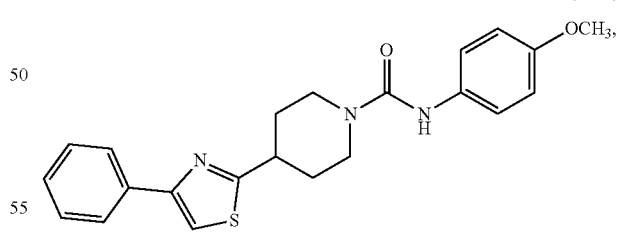

or a pharmaceutically acceptable salt or isomer thereof.

In some embodiments, a subject in need of cancer treatment is administered a therapeutically effective amount of a compound of formula II. In some embodiments, a subject in need of cancer treatment is administered a therapeutically effective amount of a compound of formula IIa. In some embodiments, a subject in need of cancer treatment is administered a therapeutically effective amount of a compound of formula IIb. In some embodiments, a subject in need of cancer treatment is administered a therapeutically effective amount of a compound that is:
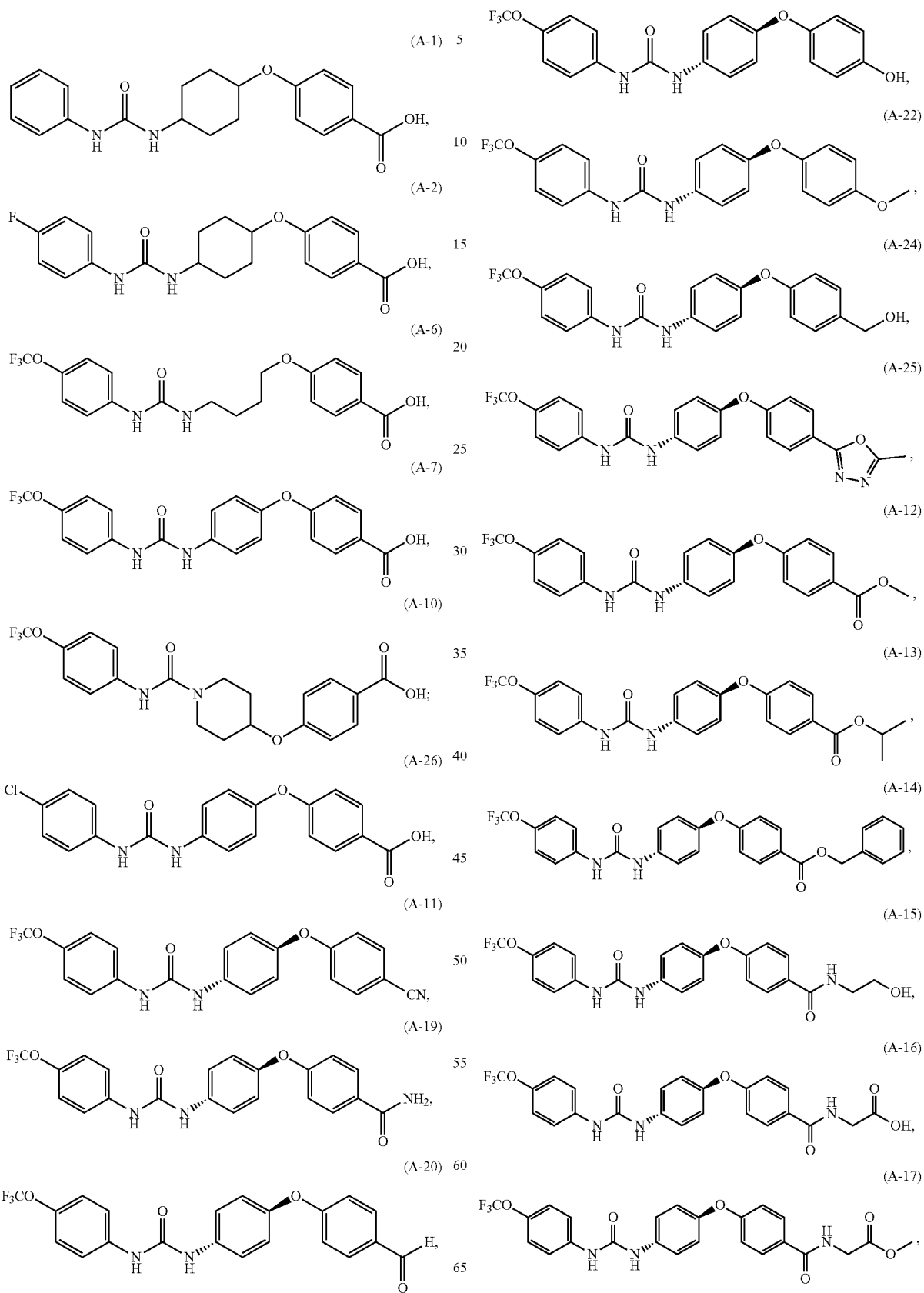

-continued

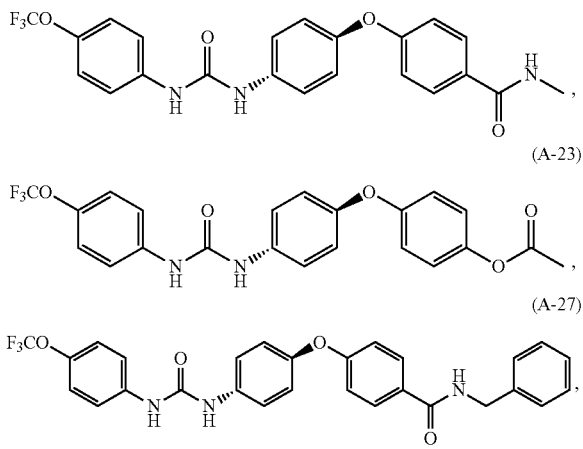

or a pharmaceutically acceptable salt or isomer thereof.

VII. EXAMPLES

Example structures below are named according to standard IUPAC nomenclature using the CambridgeSoft ChemDraw naming package. Compounds A-3 and A-26 (Ulu (2012) Br. J. Pharmacol. 165:1401); A-4 (PCT International Application No. WO 2006/045119); t-TUCB and A-5 (Hwang (2007) J. Med. Chem. 50:3825); A-7 (PCT International Application No. WO 2008/116145); A-16 (PCT International Application No. WO 2013/138118); and A11 and A18 (PCT International Application WO 2012/112570) were prepared as described previously in the respective cited references.

Example 1. A-1. 4-((trans-4-(3-phenylureido)cyclohexyl)oxy)benzoic acid

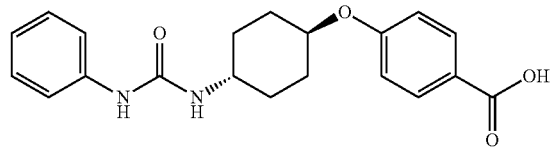 [SMILES: O=C(Nc1ccccc1)N[C@H]1CC[C@H](Oc2ccc(C(=O)O)cc2)CC1]

The starting material (4-((trans-4-aminocyclohexyl)oxy) benzoic acid) was prepared as previously described (Hwang et al, (2013) Bioorg. Med. Chem. Lett., 23:3732). To a solution of 4-((trans-4-aminocyclohexyl)oxy)benzoic acid (121 mg, 0.51 mmol) in dimethyl formamide (DMF, 10 mL) was added phenyl isocyanate (82 mg, 0.69 mmol). The reaction was allowed to stir overnight at which point ethyl acetate (EtOAc) and a solution of 1 M $Na_2CO_3$ was added and the aqueous layer was separated. A solution of 1 N HCl was added to the aqueous layer until pH=2 and the precipitates were filtered. The resulting product (103 mg, 0.29 mmol, 57%) was used without further purification. Melting point (MP)=241.2-252.9 (244.0°) C 1H NMR (400 MHz, DMSO-d6) δ 12.60 (s, 1H), 8.29 (s, 1H), 7.87 (d, J=8.5 Hz, 2H), 7.37 (d, J=8.0 Hz, 2H), 7.21 (t, J=7.7 Hz, 2H), 7.02 (d, J=8.6 Hz, 2H), 6.87 (t, J=7.4 Hz, 1H), 6.13 (d, J=7.5 Hz, 1H), 4.49-4.41 (b, 1H), 3.57-3.50 (b, 1H), 2.05 (d, J=11.4 Hz, 2H), 1.94 (d, J=10.5 Hz, 2H), 1.49 (q, J=10.5 Hz, 2H), 1.36 (q, J=10.5 Hz, 2H).

Example 2. A-2. 4-((trans-4-(3-(4-fluorophenyl)ureido)cyclohexyl)oxy)benzoic acid

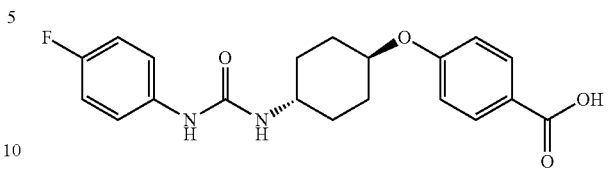

The starting material (4-((trans-4-aminocyclohexyl)oxy) benzoic acid) was prepared as previously described (Hwang et al, (2013) Bioorg. Med. Chem. Lett., 23:3732). To a solution of 4-((trans-4-aminocyclohexyl)oxy)benzoic acid (128 mg, 0.54 mmol) in DMF (10 mL) was added 4-fluorophenyl isocyanate (81 mg, 0.59 mmol). The reaction was allowed to stir overnight at which point EtOAc and a solution of 1 M $Na_2CO_3$ was added and the aqueous layer was separated. A solution of 1 N HCl was added to the aqueous layer until pH=2 and the precipitates were filtered. The resulting product (47 mg, 0.13 mmol, 23% yield) was used without further purification. MP=237.1-248.6 (242.3°) C 1H NMR (400 MHz, DMSO-d6) δ 12.58 (s, 1H), 8.56 (s, 1H), 7.84 (d, J=8.8 Hz, 2H), 7.36 (dd, J=9.1, 5.0 Hz, 2H), 7.07-6.96 (m, 4H), 6.27 (d, J=7.6 Hz, 1H), 4.46-4.39 (m, 1H), 3.55-3.46 (m, 1H), 2.02 (d, J=12.4 Hz, 2H), 1.90 (d, J=13.1 Hz, 2H) 1.50-1.29 (m, 4H).

Example 3. A-6. 4-(4-(3-(4-(trifluoromethoxy)phenyl)ureido)butoxy)benzoic acid

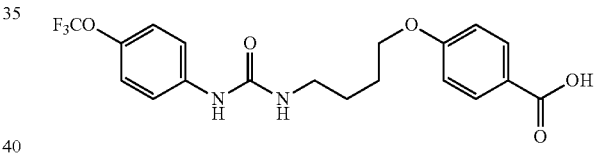

To a flask containing 4-aminobutanol (1.035 g, 11.6 mmol) in tetrahydrofuran (THF, 100 mL) was added 4-trifluoromethoxyphenyl isocyanate (2.516 g, 12.4 mmol) dropwise. The reaction was allowed to stir overnight and was quenched by the addition of 0.1 M HCl (50 mL). The product was extracted with EtOAc (100 mL), dried over $MgSO_4$ and evaporated. The resulting solid was crystallized in EtOAc/methanol (MeOH), filtered and the filtrate was crystallized again in Hexane/EtOAc. The combined solids were collected to yield 1-(4-hydroxybutyl)-3-(4-(trifluoromethoxy)phenyl)urea without further purification (2.550 g, 8.7 mmol, 75% yield). MP=117.2-117.9° C. (117.9° C.) 1H 400 MHz NMR (DMSO-$d_6$): 8.62 (s, 1H), 7.48 (d, J=8.8 Hz, 2H), 7.20 (d, J=8.8 Hz, 2H), 6.17 (t, J=5.6 Hz, 1H), 3.40 (t, J=6.0 Hz, 2H), 3.08 (q, J=6.0 Hz, 2H), 1.44 (t, J=6.8 Hz, 4H).

To a solution containing 1-(4-hydroxybutyl)-3-(4-(trifluoromethoxy)phenyl)urea (776 mg, 2.7 mmol) in DMF (40 mL) at 0° C., NaH (60% in mineral oil, 231 mg, 5.8 mmol) was added 50 mg at a time. The solution was allowed to stir for 1 hour, after which 4-fluorobenzonitrile (553 mg, 4.6 mmol) was added. After 2 hr, additional NaH (108 mg, 2.7 mmol) was added. After stirring overnight, the product was precipitated by addition of water and the product was filtered and dried in the vacuum to provide 1-(4-(4-cyanophenoxy) butyl)-3-(4-(trifluoromethoxy)phenyl)urea (992 mg, 2.5 mmol, 93% yield). MP=123.1-129.4° C. (125.0° C.)¹H NMR (400 MHz, DMSO-d₆) δ 8.67, 7.75 (d, J=7.2 Hz, 2H), 7.48 (d, J=9.2, 2H), 7.21 (d, J=8.4 Hz, 2H), 7.10 (d, J=9.2, 2H), 6.27 (t, J=5.6, 1H), 4.08 (t, J=6.4 Hz, 2H), 3.15 (q, J=6.5 Hz, 2H), 1.78-1.71 (m, 2H), 1.61-1.54 (m, 2H).

To a solution of 1-(4-(4-cyanophenoxy)butyl)-3-(4-(trifluoromethoxy)phenyl)urea (179 mg, 0.46 mmol) in ethanol (EtOH, 30 mL) was added a 6 N solution of NaOH (2 mL). The reaction was stirred at room temperature. After 8 days, the reaction was heated to 60° C. and stirred for an additional 4 days. The ethanol was evaporated from the reaction and ether and H₂O were added to the flask. The product precipitated between the layers and filtered off to afford the product (45 mg, 0.11 mmol, 24%). MP=240.6-247.2° C. (242.8° C.)¹H NMR (400 MHz, DMSO-d₆) δ 10.57 (s, 1H), 8.17 (s, 1H), 7.81 (d, J=7.1 Hz, 2H), 7.62 (d, J=8.9 Hz, 2H), 7.17 (d, J=8.7 Hz, 2H), 6.79 (d, J=8.3 Hz, 2H), 3.97 (t, J=6.7 Hz, 2H), 3.18-3.10 (m, 2H), 1.79-1.70 (m, 2H), 1.66 (s, 1H), 1.62-1.52 (m, 2H).

Example 4. A-10. 4-((1-((4-(trifluoromethoxy)phenyl)carbamoyl)piperidin-4-yl)oxy)benzoic acid

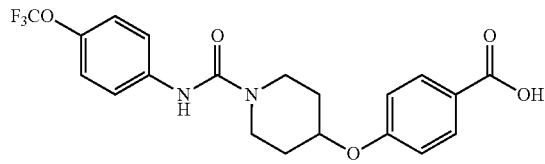 [SMILES: O=C(O)c1ccc(OC2CCN(C(=O)Nc3ccc(OC(F)(F)F)cc3)CC2)cc1]

To a solution of 4-hydroxypiperidine (4.93 g, 48.8 mmol) in DMF (150 mL) at 0° C., NaH was added (60% in oil, 2.27 g, 59.3 mmol). After stirring for 1 h at 0° C., 4-fluorobenzonitrile (7.20 g, 59.5 mmol) was added and the reaction was heated to 60° C. for 1 hour. The reaction was then cooled to room temperature and allowed to stir overnight, at which point water was used to quench the reaction. EtOAc was used to extract the product and after separation from the aqueous layer, was mixed with equal volume of 1 N HCl. The aqueous layer was collected, neutralized by addition of NaOH and the product was extracted with EtOAc. The organic layer was dried with MgSO₄ and evaporated to afford 4-(piperidin-4-yloxy)benzonitrile (3.17 g, 15.7 mmol, 32% yield). MP=77.7-85.2° C. (80.6° C.) ¹H NMR (300 MHz, DMSO-d₆) δ 7.79-7.65 (m, 2H), 7.17-7.05 (m, 2H), 4.58 (s, 1H), 4.24 (s, 2H), 2.69 (d, J=26.1 Hz, 2H), 2.01-1.85 (m, 2H), 1.49 (dp, J=14.1, 5.5, 4.7 Hz, 2H).

To a solution of 4-(piperidin-4-yloxy)benzonitrile (669 mg, 3.7 mmol) in THF (25 mL), 4-trifluoromethoxyphenyl isocyanate (750 mg, 3.7 mmol) was added and the solution was allowed to stir overnight. The reaction was stopped by addition of 0.1 M HCl and extracted with EtOAc. The organic phase was collected, dried over MgSO4 and evaporated. The product was purified by flash chromatography with 1:1 Hexane:EtOAc to afford the production of 4-(4-cyanophenoxy)-N-(4-(trifluoromethoxy)phenyl)piperidine-1-carboxamide (790 mg, 2.0 mmol, 53% yield). MP=119.9-121.6° C. (120.8° C.) ¹H 400 MHz NMR (DMSO-d₆): 8.56 (s, 1H), 7.76 (d, J=8.8 Hz, 2H), 7.45 (d, J=8.4 Hz, 2H), 7.22 (t, J=7.6 Hz, 2H), 7.17 (d, J=8.8 Hz, 2H), 6.92 (t, J=7.6 Hz, 1H), 4.79-4.73 (b, 1H), 3.85-3.82 (b, 2H), 3.28 (t, J=11.2 Hz, 2H), 2.00-1.97 (b, 2H), 1.63-1.56 (b, 2H).

To a solution of 4-(4-cyanophenoxy)-N-(4-(trifluoromethoxy)phenyl)piperidine-1-carboxamide (790 mg, 2.0 mmol) in EtOH (25 mL), 6 N NaOH was added (10 mL) and the reaction was heated to 80° C. for 10 hours. The resulting mixture was concentrated by rotary evaporation and the aqueous solution as diluted with additional water and extracted with EtOAc. The aqueous layer was collected, acidified with 1 N HCl and extracted again with EtOAc. The organic layer was collected, dried over MgSO₄ and evaporated. The resulting solid was recrystallized in MeOH and 1 N HCl to provide the product (261 mg, 0.62 mmol, 32% yield.). MP=219.3-223.0° C. (220.5° C.) ¹H 400 MHz NMR (DMSO-d₆): 12.63 (s, 1H), 8.77 (s, 1H), 7.89 (d, J=8.8 Hz, 2H), 7.56 (d, J=9.2 Hz, 2H), 7.23 (d, J=8.4 Hz, 2H), 7.07 (d, J=8.8 Hz, 2H), 4.75-4.70 (b, 1H), 3.85-3.82 (b, 2H), 3.33-3.28 (b, 2H), 2.02-1.98 (b, 2H), 1.62-1.57 (b, 2H).

Example 5. A-12. methyl 4-((trans-4-(3-(4-(trifluoromethoxy)phenyl)ureido)cyclohexyl)oxy) benzoate

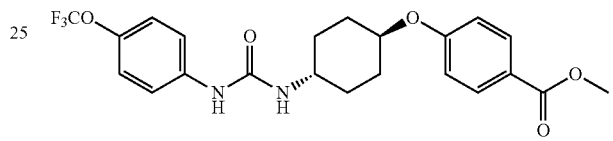

MP=206.2-209.1° C. (207.2° C.)¹H NMR (600 MHz, DMSO-d₆) δ 8.51 (s, 1H), 7.88 (d, J=9 Hz, 2H), 7.46 (d, J=9 Hz, 2H), 7.21 (d, J=9 Hz, 2H), 7.05 (d, J=9 Hz, 2H), 6.20 (d, J=8 Hz, 1H), 4.50-4.44 (m, 1H), 3.80 (s, 3H), 3.56-3.49 (m, 1H), 2.08-2.02 (m, 2H), 1.96-1.90 (m, 2H), 1.54-1.46 (m, 2H), 1.41-1.33 (m, 2H).

Example 6. A-13. isopropyl 4-((trans-4-(3-(4-(trifluoromethoxy)phenyl)ureido)cyclohexyl)oxy)benzoate

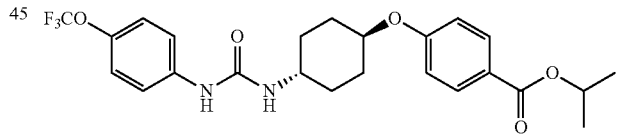

To a solution of t-TUCB (320 mg, 0.73 mmol) in isopropyl alcohol (50 mL) was added concentrated H₂SO₄ (100 mg). The solution was stirred for 14 days after which a saturated solution of NaHCO₃ and EtOAc were added. The aqueous layer was extracted and washed two additional times with saturated NaHCO₃. The organic layer was dried over MgSO4, evaporated, and purified by flash chromatography with 100% EtOAc yielding the product (57 mg, 0.12 mmol, 16%). MP=184.4-190.6° C. (186.4° C.)¹H NMR (300 MHz, DMSO-d₆) δ 8.53 (s, 1H), 7.88 (d, J=8.7 Hz, 2H), 7.48 (d, J=9.0 Hz, 2H), 7.22 (d, J=8.6 Hz, 2H), 7.06 (d, J=9.0 Hz, 2H), 6.21 (d, J=7.7 Hz, 1H), 5.10 (p, J=6.2 Hz, 1H), 4.48 (s, 1H), 3.54 (s, 1H), 2.06 (d, J=11.3 Hz, 2H), 1.95 (d, J=12.5 Hz, 2H), 1.64-1.22 (m, 13H).

Example 7. A-14. benzyl 4-((trans-4-(3-(4-(trifluoromethoxy)phenyl)ureido)cyclohexyl)oxy) benzoate

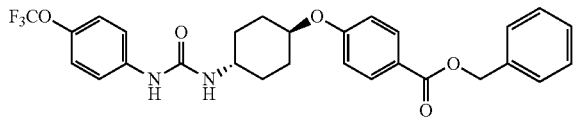 [SMILES: O=C(Nc1ccc(OC(F)(F)F)cc1)N[C@H]1CC[C@H](Oc2ccc(C(=O)OCc3ccccc3)cc2)CC1]

t-TUCB (245 mg, 0.56 mmol), benzyl alcohol (200 uL, 1.93 mmol), 1-ethyl-3-dimethylaminopropyl)carbodiimide (EDCI, 148 mg, 0.95 mmol), 4-dimethylaminopyridine (DMAP, 5 mg, 0.04 mmol) and trimethylamine (Et$_3$N, 63 mg, 0.62 mmol) were dissolved in THF and stirred overnight. The product was extracted twice with a saturated solution of NaHCO$_3$ and once with 1 M HCl. The product was dried over MgSO$_4$, evaporated and purified by flash chromatography with 100% EtOAc. The final product was recrystallized in EtOAc (34 mg, 0.06 mmol, 11%). MP=186.9-189.6° C. (188.1° C.)$^1$H NMR (400 MHz, DMSO-d$_6$) δ 8.47 (s, 1H), 7.87 (d, J=8.9 Hz, 2H), 7.47-7.26 (m, 6H), 7.16 (d, J=8.8 Hz, 2H), 7.02 (d, J=8.9 Hz, 1H), 6.15 (d, J=7.9 Hz, 1H), 5.26 (s, 2H), 4.41 (s, 1H), 3.47 (s, 1H), 1.99 (s, 2H), 1.88 (s, 2H), 1.45 (q, J=11.1, 10.3 Hz, 2H), 1.32 (q, J=11.2 Hz, 2H).

Example 8. A-15. N-(2-hydroxyethyl)-trans-4-((-4-(3-(4-(trifluoromethoxy)phenyl)ureido) cyclohexyl) oxy)benzamide

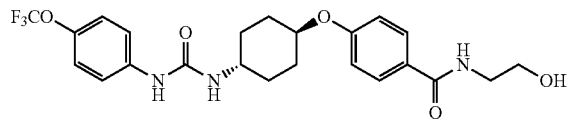 [SMILES: O=C(Nc1ccc(OC(F)(F)F)cc1)N[C@H]1CC[C@H](Oc2ccc(C(=O)NCCO)cc2)CC1]

To a solution of t-TUCB (0.31 g, 0.80 mmol) in 6 mL THF, benzotriazol-1-yl-oxytripyrrolindinophosphonium hexafluorophosphate (PyBOP) (0.24 g, 0.65 mmol), ethanolamine (0.37 g, 6.0 mmol), and triethylamine (0.62 g, 6.1 mmol) were added. The mixture was stirred overnight at room temperature. Reaction mixture was diluted with EtOAc and washed with saturated NaHCO$_3$ three times. After drying the organic layer with MgSO$_4$, the solvent was evaporated and the crude product was used without further purification. MP=186.9-194.5° C. (189.5° C.)$^1$H NMR (400 MHz): 8.47 (s, 1H), 8.22 (t, 1H, J=5.6 Hz), 7.75 (d, 2H, J=8.8 Hz), 7.42 (d, 2H, J=9.2 Hz), 7.17 (d, 2H, J=8.8 Hz), 6.94 (d, 2H, J=8.8 Hz), 6.15 (d, 1H, J=7.6 Hz), 4.67 (t, 1H, J=5.6 Hz), 4.38 (m, 1H), 3.25 (9, 2H, J=6.4 Hz) 3.05-2.93 (m, 3H), 2.04-1.96 (m, 2H), 1.92-1.84 (m, 2H), 1.44 (9, 2H, J=12 Hz), 1.32 (9, 2H, J=12 Hz).

Example 9. A-17. methyl trans-(4-((4-(3-(4-(trifluoromethoxy)phenyl)ureido)cyclohexyl) oxy)benzoyl) glycinate

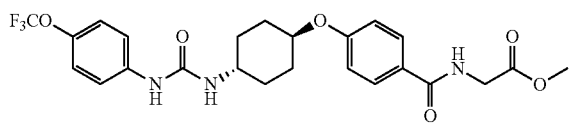 [SMILES: COC(=O)CNC(=O)c1ccc(O[C@H]2CC[C@H](NC(=O)Nc3ccc(OC(F)(F)F)cc3)CC2)cc1]

MP=207.5-213.2° C. (208.3° C.)$^1$H NMR (600 MHz, DMSO-d$_6$) δ 8.78 (t, J=6 Hz, 1H), 8.51 (s, 1H), 7.82 (d, J=8 Hz, 2H), 7.47 (d, J=8 Hz, 2H), 7.22 (d, J=8 Hz, 2H), 7.03 (d, J=8 Hz, 2H), 6.20 (d, J=8 Hz, 1H), 4.48-4.41 (m, 1H), 3.98 (d, J=6 Hz, 2H), 3.65 (s, 3H), 3.57-3.48 (m, 1H), 2.10-2.01 (m, 2H), 1.96-1.89 (m, 2H), 1.54-1.32 (m, 4H).

Example 10. A-19. trans-4-((-4-(3-(4-(trifluoromethoxy)phenyl)ureido)cyclohexyl)oxy) benzamide

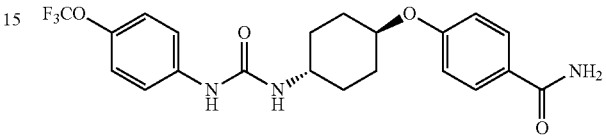

MP=232.9-234.4° C. (233.2° C.)$^1$H NMR (300 MHz, DMSO-d$_6$) δ 8.66 (s, 1H), 7.81 (d, J=8.8 Hz, 3H), 7.48 (d, J=9.1 Hz, 2H), 7.21 (d, J=8.6 Hz, 2H), 7.15 (s, 1H), 6.98 (d, J=8.8 Hz, 2H), 6.33 (d, J=7.7 Hz, 1H), 4.42 (q, J=6.2, 5.6 Hz, 1H), 3.53 (d, J=7.4 Hz, 1H), 2.05 (d, J=11.9 Hz, 2H), 1.93 (d, J=11.8 Hz, 2H), 1.43 (dp, J=23.7, 11.9, 11.2 Hz, 4H).

Example 11. A-20, trans-1-(4-(4-formyl-phenoxy)cyclohexyl)-3-(4-(trifluoromethoxy) phenyl)urea

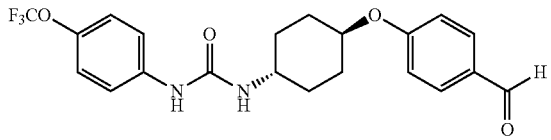 [SMILES: O=Cc1ccc(O[C@H]2CC[C@H](NC(=O)Nc3ccc(OC(F)(F)F)cc3)CC2)cc1]

To a solution of trans-1-(4-(4-cyano-phenoxy)cyclohexyl)-3-(4-(trifluoromethoxy)phenyl)urea (1.63 g, 3.9 mmol) in THF (100 mL), diisobutyl aluminum hydride (DIBAL-H) (4 mL of 1 M solution in Hexanes) was added. After an hour, an additional 8 mL of DIBAL-H was added. After a second hour, another 8 mL of DIBAL-H was added. 4 hours after the initial start of the reaction, a solution of Rochelle's Salt (sodium potassium tartrate, 0.25M) was added dropwise on ice until 5 mL at which point 100 mL was added. EtAcO was added to the resulting mixture and the resulting organic layer was extracted and washed with brine and water. The solution was then dried with MgSO$_4$, evaporated to 50 mL, filtered on a bed of silica, and evaporated to dryness to yield the product (960 mg, 2.3 mmol, 59% yield). MP=140.9-148.3° C. (144.6° C.)$^1$H NMR (400 MHz, DMSO-d$_6$) δ 9.85 (s, 1H), 8.51 (s, 1H), 7.84 (d, J=8.9 Hz, 1H), 7.46 (d, J=9.1 Hz, 2H), 7.20 (d, J=8.5 Hz, 2H), 7.13 (d, J=8.5 Hz, 1H), 6.21 (d, J=7.5 Hz, 1H), 4.56-4.47 (m, 1H), 3.53 (s, 1H), 2.06 (d, J=10.9 Hz, 2H), 1.93 (d, J=11.1 Hz, 2H), 1.51 (q, J=12.2 Hz, 2H), 1.38 (q, J=11.2, 10.4 Hz, 2H).

Example 12. A-21. trans-1-(4-(4-hydroxy-phenoxy)cyclohexyl)-3-(4-(trifluoromethoxy) phenyl)urea

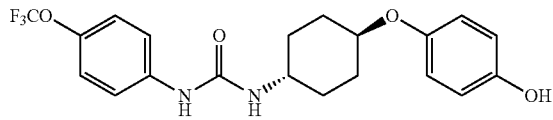 [SMILES: O=C(Nc1ccc(OC(F)(F)F)cc1)N[C@H]1CC[C@H](Oc2ccc(O)cc2)CC1]

To a solution of trans-1-(4-(4-formyl-phenoxy)cyclohexyl)-3-(4-(trifluoromethoxy)phenyl)urea (344 mg, 0.82 mmol) in dichloromethane (DCM, 30 mL), meta-chloroperoxybenzoic acid (mCPBA) was added (316 mg of 70-75% with water) and allowed to stir overnight. The reaction was quenched by addition of a saturated solution of $Na_2SSO_3$. The organic layer was then extracted, washed with $NaHCO_3$, dried with $MgSO_4$ and evaporated to 5 mL. The resulting solution was diluted with EtOH (40 mL) and a solution of NaOH (7 mL of 6N) was added and allowed to stir for one hour. The solution was then evaporated to 10 mL and 1 N HCl was added until pH=2. Then product was then extracted with EtOAc, dried over $MgSO_4$ and evaporated to afford the product (309 mg, 0.75 mmol, 91% yield). Before determining $IC_{50}$, the resulting product was crystallized in $MeOH/H_2O$. MP=160.6-166.3 (162.0) ° C. $^1$H 400 MHz NMR (DMSO-$d_6$): 8.90 (s, 1H), 8.51 (s, 1H), 7.46 (d, J=9.2 Hz, 2H), 7.21 (d, J=8.8 Hz, 2H), 6.76 (d, J=9.2 Hz, 2H), 6.65 (d, J=8.4 Hz, 2H), 6.16 (d, J=8.0 Hz, 1H), 4.14-4.04 (b, 1H), 3.55-3.45 (b, 1H), 2.02-1.96 (b, 2H), 1.94-1.86 (b, 2H), 1.45-1.37 (m, 2H), 1.33-1.25 (m, 2H).

Example 13. A-22. 1-(trans-4-(4-methoxyphenoxy)cyclohexyl)-3-(4-(trifluoromethoxy) phenyl)urea

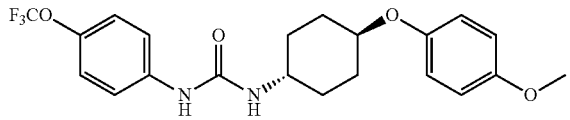 [SMILES: COc1ccc(O[C@H]2CC[C@H](NC(=O)Nc3ccc(OC(F)(F)F)cc3)CC2)cc1]

To a solution of trans-1-(-4-(4-hydroxy-phenoxy)cyclohexyl)-3-(4-(trifluoromethoxy)phenyl)urea (155 mg, 0.38 mmol) in DMF (10 mL), methyl iodide (MeI, 842 mg, 5.9 mmol) and $K_2CO_3$ (851, 6.2 mmol) were added and the reaction was allowed to stir overnight. The product was precipitated by addition of $H_2O$, filtered and washed once with 1 M $K_2CO_3$. The resulting solids were recrystallized in $MeOH/H_2O$ to afford the product (65 mg, 0.15 mmol, 40% yield). MP=180.0-184.4 (181.8°) C $^1$H NMR (400 MHz, DMSO-$d_6$) δ 8.52 (s, 1H), 7.46 (d, J=9.1 Hz, 2H), 7.21 (d, J=8.7 Hz, 2H), 6.85 (q, J=9.1 Hz, 4H), 6.18 (d, J=7.6 Hz, 1H), 4.20-4.14 (b, 1H), 3.69 (s, 3H), 3.55-3.46 (b, 1H), 2.03-1.96 (b, 2H), 1.95-1.86 (b, 2H), 1.48-1.38 (m, 2H), 1.35-1.27 (m, 2H).

Example 14. A-23. 4-((trans-4-(3-(4-(trifluoromethoxy)phenyl)ureido)cyclohexyl)oxy) phenyl acetate

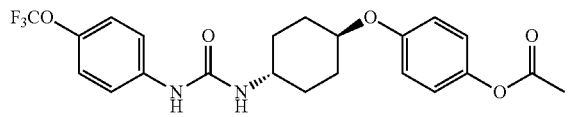 [SMILES: CC(=O)Oc1ccc(O[C@H]2CC[C@H](NC(=O)Nc3ccc(OC(F)(F)F)cc3)CC2)cc1]

To a solution of trans-1-(-4-(4-hydroxy-phenoxy)cyclohexyl)-3-(4-(trifluoromethoxy)phenyl)urea (104 mg, 0.25 mmol) in DCM (5 mL) was added acetyl chloride (71 mg, 0.90 mmol) and pyridine (23 mg, 0.29 mmol). After 30 minutes, additional pyridine (60 mg) and acetyl chloride (40 mg) were added. After an hour, the reaction mixture was diluted with EtOAc, extracted 3 times with $K_2CO_3$ (1M), dried over $MgSO_4$ and evaporated. The resulting mixture was purified by flash chromatography over a gradient of 1:1 Hexanes:EtOAc to 100% EtOAc. The product was recrystallized in Hex:EtOAc to give a light brown solid (21 mg, 0.05 mmol, 20% yield). MP=204.1-209.0° C. (206.2° C.)$^1$H NMR (400 MHz, DMSO-$d_6$) δ 8.51 (s, 1H), 7.47 (d, J=9.0 Hz, 2H), 7.21 (d, J=8.7 Hz, 2H), 6.98 (q, J=9.0 Hz, 4H), 6.19 (d, J=7.6 Hz, 1H), 4.34-4.26 (b, 1H), 3.56-3.48 (b, 1H), 2.23 (s, 3H), 2.03 (d, J=12.3 Hz, 2H), 1.92 (d, J=12.7 Hz, 2H), 1.46 (q, J=11.6 Hz, 2H), 1.34 (q, J=11.7 Hz, 2H).

Example 15. A-24. 1-(trans-4-(4-(hydroxymethyl)phenoxy)cyclohexyl)-3-(4-(trifluoromethoxy)phenyl)urea

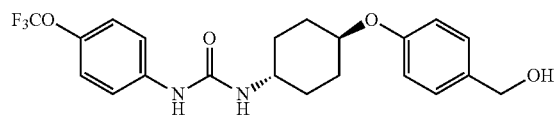 [SMILES: O=C(Nc1ccc(OC(F)(F)F)cc1)N[C@H]1CC[C@H](Oc2ccc(CO)cc2)CC1]

To a solution of t-TUCB (199 mg, 0.45 mmol) in THF (30 mL), lithium aluminum hydride (231 mg, 6.1 mmol) was added 15 mg at a time. After 14 days, 1 N HCl was added to the reaction mixture on ice and allowed to stir for 30 minutes. The resulting mixture was extracted, dried over $MgSO_4$ and evaporated. The crude mixture was purified by flash chromatography with 1:1 Hexanes:EtOAc to afford the product (65 mg, 0.15 mmol, 33%). MP=172.9-176.7° C. (174.3° C.)$^1$H NMR (300 MHz, DMSO-$d_6$) δ 8.50 (s, 1H), 7.45 (d, J=9.1 Hz, 2H), 7.19 (d, J=8.5 Hz, 4H), 6.87 (d, J=8.2 Hz, 2H), 6.16 (d, J=7.6 Hz, 1H), 5.00 (t, J=5.7 Hz, 1H), 4.38 (d, J=5.6 Hz, 2H), 4.34-4.15 (m, 1H), 3.62-3.42 (m, 1H), 2.01 (d, J=13.0 Hz, 2H), 1.92 (d, J=12.4 Hz, 2H), 1.38 (dp, J=23.3, 11.6 Hz, 4H).

Example 16. A-25. 1-(trans-4-(4-(5-methyl-1,3,4-oxadiazol-2-yl)phenoxy)cyclohexyl)-3-(4-(trifluoromethoxy)phenyl)urea

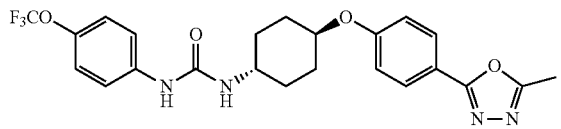 [SMILES: Cc1nnc(-c2ccc(O[C@H]3CC[C@H](NC(=O)Nc4ccc(OC(F)(F)F)cc4)CC3)cc2)o1]

To a solution of trans-1-(4-(4-formyl-phenoxy)cyclohexyl)-3-(4-(trifluoromethoxy)phenyl)urea (438 mg, 1.0 mmol) in EtOH (50 mL) was added acethydrazide (120 mg, 1.5 mmol). After stirring for 1 hour, the solvent was evaporated and the product was reconstituted in DMSO (50 mL). $K_2CO_3$ (626 mg, 4.5 mmol) and $I_2$ (567 mg, 2.2 mmol) were added to the reaction and allowed to stir for 2 additional hours. The reaction was quenched with EtOAc, washed twice with saturated $NaHCO_3$, dried over $MgSO_4$, evaporated and purified by column chromatography with 100%

EtOAc. The product was isolated as a white solid (50 mg, 0.11 mmol, 11% yield). MP=227.6-231.9° C. (229.1° C.)¹H NMR (300 MHz, DMSO-d$_6$) δ 8.52 (s, 1H), 7.88 (d, J=8.8 Hz, 2H), 7.48 (d, J=9.0 Hz, 2H), 7.27-7.19 (m, 2H), 7.15 (d, J=8.9 Hz, 2H), 6.21 (d, J=7.6 Hz, 1H), 4.56-4.42 (m, 1H), 3.55 (d, J=10.2 Hz, 1H), 2.56 (s, 3H), 2.08 (d, J=12.0 Hz, 2H), 1.96 (d, J=11.0 Hz, 2H), 1.46 (dq, J=41.3, 11.4 Hz, 4H).

Example 17. A-27. N-benzyl-trans-4-((-4-(3-(4-(trifluoromethoxy)phenyl)ureido)cyclohexyl)oxy)benzamide

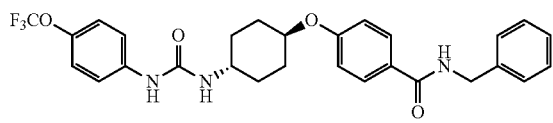 [SMILES: O=C(Nc1ccc(OC(F)(F)F)cc1)N[C@H]1CC[C@H](Oc2ccc(C(=O)NCc3ccccc3)cc2)CC1]

Benzylamine hydrochloride (208 mg, 1.5 mmol), t-TUCB (403 mg, 0.92 mmol), Et$_3$N (335 mg, 3.3 mmol) and PyBop (613 mg, 1.2 mmol) were combined in THF (30 mL). After stirring overnight, the reaction mixture was diluted with EtOAc (30 mL) and extracted 3 times with saturated NaHCO$_3$, extracted 3 times with 1 M HCl, dried over MgSO$_4$, and evaporated. The product was recrystallized in MeOH and H$_2$O to afford a white solid (296 mg, 0.56 mmol, 61%). MP=237.7-239.7° C. (238.6° C.)¹H NMR (300 MHz, DMSO-d$_6$) δ 8.88 (t, J=6.0 Hz, 1H), 8.52 (s, 1H), 7.86 (d, J=8.7 Hz, 2H), 7.48 (d, J=9.0 Hz, 2H), 7.39-7.26 (m, 4H), 7.22 (d, J=8.5 Hz, 2H), 7.02 (d, J=8.5 Hz, 2H), 6.20 (d, J=7.6 Hz, 1H), 4.47 (d, J=6.0 Hz, 3H), 3.54 (d, J=9.8 Hz, 1H), 2.07 (d, J=10.7 Hz, 2H), 1.95 (d, J=12.1 Hz, 2H), 1.44 (dq, J=37.6, 10.9 Hz, 4H).

Example 18. B-1. N-(4-fluorophenyl)-4-(quinolin-3-ylmethyl)piperidine-1-carboxamide

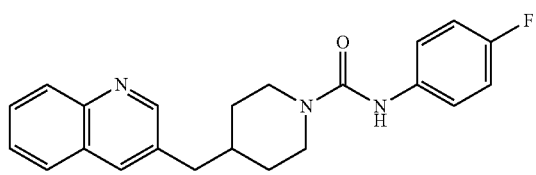 [SMILES: O=C(Nc1ccc(F)cc1)N1CCC(Cc2cnc3ccccc3c2)CC1]

4-fluorophenyl isocyanate (73 mg, 0.53 mmol) was added to a solution of 3-(piperidin-4-ylmethyl)quinolone (Ahn et al. (2007) Biochemistry, 13:13019, 140 mg, 0.62 mmol) dissolved in THF (10 mL) and stirred overnight. The reaction was quenched with 1 N HCl (10 mL) and stirred for 5 minutes. The reaction was neutralized by addition of Na$_2$CO$_3$ and extracted three times with EtOAc. The product was run on a column of 100% EtOAc yielding the product (165 mg, 0.45 mmol, 86%). MP=160.9-164.3° C. (162.2° C.)¹H NMR (400 MHz, DMSO-d$_6$) δ 8.77 (s, 1H), 8.47 (s, 1H), 8.11 (s, 1H), 7.98 (d, J=8.4 Hz, 1H), 7.90 (d, J=7.9 Hz, 1H), 7.68 (t, J=7.0 Hz, 1H), 7.56 (t, J=7.5 Hz, 1H), 7.43 (dd, J=9.1, 5.1 Hz, 2H), 7.03 (t, J=8.9 Hz, 2H), 4.08 (d, J=13.3 Hz, 2H), 2.73-2.67 (m, 4H), 1.87-1.81 (m, 1H), 1.59 (d, J=11.3 Hz, 2H), 1.15 (q, J=12.3, 11.7 Hz, 2H).

Example 19. B-2. N-(4-chlorophenyl)-4-(quinolin-3-ylmethyl)piperidine-1-carboxamide

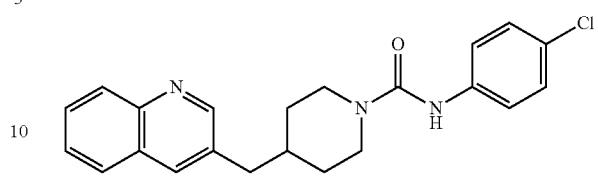

MP=167.0-173.6° C. (172.0° C.). ¹H NMR (300 MHz, DMSO-d$_6$) δ 8.79 (d, J=2.2 Hz, 1H), 8.57 (s, 1H), 8.14 (s, 1H), 7.99 (d, J=8.4 Hz, 1H), 7.92 (d, J=8.1 Hz, 1H), 7.70 (ddd, J=8.2, 7.0, 1.3 Hz, 1H), 7.58 (ddd, J=8.1, 6.8, 1.3 Hz, 1H), 7.55-7.41 (m, 2H), 7.36-7.19 (m, 2H), 4.10 (d, J=13.3 Hz, 2H), 2.74 (t, J=11.0 Hz, 4H), 1.87 (s, 1H), 1.63 (d, J=13.0 Hz, 2H), 1.32-1.04 (m, 2H).

Example 20. B-3. N-(2-fluorophenyl)-4-(quinolin-3-ylmethyl)piperidine-1-carboxamide

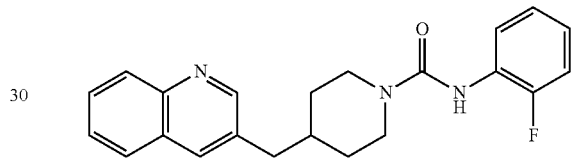

2-fluorophenyl isocyanate (85 mg, 0.62 mmol) was added to a solution of 3-(piperidin-4-ylmethyl)quinolone (151 mg, 0.67 mmol) dissolved in THF (10 mL) and stirred overnight. The reaction was quenched with 1 N HCl (10 mL) and stirred for 5 minutes. The reaction was neutralized by addition of Na$_2$CO$_3$ and extracted three times with EtOAc. The product was run on a column of 100% EtOAc yielding the product (93 mg, 0.26 mmol, 41%). MP=114.1-116.8° C. (114.8° C.)¹H NMR (300 MHz, DMSO-d$_6$) δ 8.80 (d, J=2.2 Hz, 1H), 8.21 (s, 1H), 8.15 (d, J=1.7 Hz, 1H), 8.00 (d, J=8.4 Hz, 1H), 7.94 (dd, J=8.3, 1.5 Hz, 1H), 7.71 (td, J=7.0, 0.9 Hz, 1H), 7.59 (td, J=8.0, 1.3 Hz, 1H), 7.46-7.36 (m, 1H), 7.21-7.05 (m, 3H), 4.08 (d, J=13.3 Hz, 2H), 2.84-2.69 (m, 4H), 1.88 (dt, J=7.3, 3.6 Hz, 1H), 1.63 (d, J=13.3 Hz, 2H), 1.20 (qd, J=12.6, 11.9, 3.6 Hz, 2H).

Example 21. B-4. 4-(quinolin-3-ylmethyl)-N-(4-(trifluoromethoxy)phenyl)piperidine-1-carboxamide

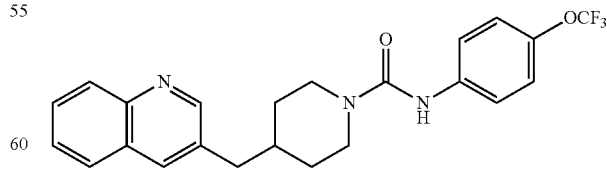

4-trifluoromethoxyphenyl isocyanate (95 mg, 0.47 mmol) was added to a solution of 3-(piperidin-4-ylmethyl)quinolone (140 mg, 0.62 mmol) dissolved in THF (10 mL) and stirred overnight. The reaction was quenched with 1 N HCl (10 mL) and stirred for 5 minutes. The reaction was neutralized by addition of Na₂CO₃ and extracted three times with EtOAc. The product was run on a column of 100% EtOAc yielding the product (190 mg, 0.44 mmol, 94%). MP=137.9-140.3° C. (138.8° C.)¹H NMR (300 MHz, DMSO-d₆) δ 8.78 (d, J=2.2 Hz, 1H), 8.64 (s, 1H), 8.13 (d, J=2.1 Hz, 1H), 7.99 (d, J=8.9 Hz, 1H), 7.91 (d, J=8.2 Hz, 1H), 7.70 (td, J=7.3, 1.6 Hz, 1H), 7.61-7.51 (m, 3H), 7.21 (d, J=9.0 Hz, 2H), 4.10 (d, J=13.2 Hz, 2H), 2.81-2.68 (m, 4H), 1.95-1.78 (m, 1H), 1.62 (d, J=11.0 Hz, 2H), 1.17 (qd, J=12.5, 4.1 Hz, 2H).

Example 22. B-5. N-(4-methoxyphenyl)-4-(quinolin-3-ylmethyl)piperidine-1-carboxamide

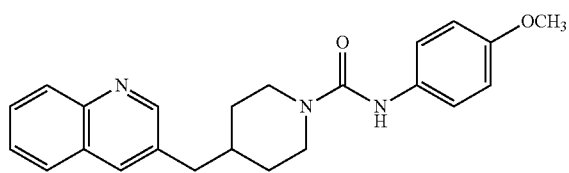 [SMILES: COc1ccc(NC(=O)N2CCC(Cc3cnc4ccccc4c3)CC2)cc1]

4-methoxyphenyl isocyanate (85 mg, 0.57 mmol) was added to a solution of 3-(piperidin-4-ylmethyl)quinolone (140 mg, 0.62 mmol) dissolved in THF (10 mL) and stirred overnight. The reaction was quenched with 1 N HCl (10 mL) and stirred for 5 minutes. The reaction was neutralized by addition of Na₂CO₃ and extracted three times with EtOAc. The product was run on a column of 100% EtOAc yielding the product (173 mg, 0.46 mmol, 81%). MP=150.2-151.8° C. (150.9° C.)¹H NMR (400 MHz, DMSO-d₆) δ 8.78 (s, 1H), 8.29 (s, 1H), 8.12 (s, 1H), 8.00 (d, J=8.4 Hz, 1H), 7.92 (d, J=8.2 Hz, 1H), 7.70 (t, J=7.6 Hz, 1H), 7.58 (t, J=7.5 Hz, 1H), 7.33 (d, J=8.9 Hz, 2H), 6.80 (d, J=9.1 Hz, 1H), 4.09 (d, J=13.3 Hz, 2H), 3.69 (s, 3H), 2.74-2.66 (m, 4H), 1.88-1.80 (m, 1H), 1.60 (d, J=12.8 Hz, 2H), 1.16 (q, J=11.9 Hz, 2H).

Example 23. B-6. N-(pyridin-3-yl)-4-(quinolin-3-ylmethyl)piperidine-1-carboxamide 3-pyridinyl isocyanate (85 mg, mmol) was added to a solution of 3-(piperidin-4-ylmethyl)quinolone (150 mg, mmol) dissolved in THF (10 mL) and stirred overnight. The reaction was quenched with 1 N HCl (10 mL) and stirred for 5 minutes. The reaction was neutralized by addition of Na₂CO₃ and extracted three times with EtOAc. The product was run on a column of 9:1 DCM:MeOH yielding the product as an off-white solid (mg, mmol, %). MP=181.4-190.9° C. (188.2° C.)¹H NMR (300 MHz, DMSO-d₆) δ 8.78 (d, J=2.2 Hz, 1H), 8.67-8.59 (m, 2H), 8.12 (dd, J=4.6, 1.5 Hz, 2H), 7.99 (d, J=7.8 Hz, 1H), 7.91 (d, J=8.2 Hz, 1H), 7.86 (ddd, J=8.4, 2.6, 1.5 Hz, 1H), 7.70 (ddd, J=8.4, 6.8, 1.5 Hz, 1H), 7.58 (ddd, J=8.1, 6.8, 1.3 Hz, 1H), 7.23 (dd, J=8.0, 4.6 Hz, 1H), 4.11 (d, J=13.6 Hz, 2H), 2.74 (dd, J=8.8, 4.6 Hz, 4H), 1.96-1.79 (m, 1H), 1.62 (d, J=11.5 Hz, 2H), 1.18 (qd, J=12.2, 3.9 Hz, 2H).

Example 24. B-7. N-(4-methoxyphenyl)-4-(quinolin-2-ylmethyl)piperidine-1-carboxamide

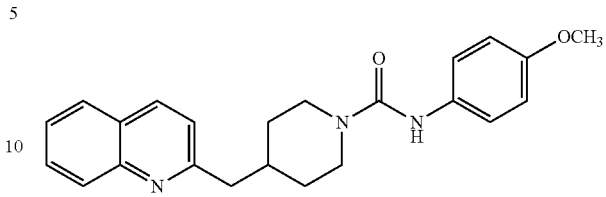

To a solution of 2-(piperidin-4-ylmethyl)quinolone (171 mg, 0.76 mmol) was dissolved in THF (10 mL) was added 4-trifluoromethoxyphenyl isocyanate (142 mg, 0.95 mmol). The solution was allowed to stir overnight and the reaction was quenched by addition of 1 N HCl (5 mL). The reaction was neutralized by adding to sat. NaHCO₃, the product was extracted with EtOAc, dried over NaSO₄ and evaporated. The product was purified by flash chromatography on a column of 1:1 Hex:EtOAc to 100% EtOAc to provide the product as a clear oil that crystallized to a white solid (69 mg, 0.18 mmol, 24% yield). MP=103.9-108.8° C. (105.4° C.)¹H NMR (300 MHz, DMSO-d₆) δ 8.25 (d, J=8.4 Hz, 2H), 7.92 (t, J=7.6 Hz, 2H), 7.77-7.64 (m, 1H), 7.53 (t, J=7.8 Hz, 1H), 7.42 (d, J=8.4 Hz, 1H), 7.30 (d, J=9.0 Hz, 2H), 6.78 (d, J=9.0 Hz, 2H), 4.07 (q, J=5.4 Hz, 2H), 3.67 (s, 3H), 2.85 (d, J=7.1 Hz, 2H), 2.71 (t, J=12.6 Hz, 2H), 2.15-1.97 (m, 1H), 1.60 (d, J=12.5, 3.5 Hz, 2H), 1.19 (qd, J=12.5, 3.5 Hz, 2H).

Example 25. B-8. N-(4-methoxyphenyl)-4-(naphthalen-2-ylmethyl)piperidine-1-carboxamide

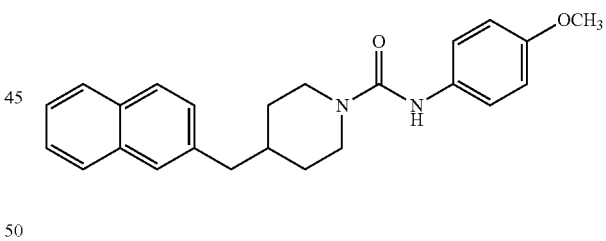

To a solution of 4-(naphthalen-2-ylmethyl)piperidine (98 mg, 0.44 mmol) in THF (10 mL) was added 4-trifluoromethoxyphenyl isocyanate (41 mg, 0.28 mmol). After stirring overnight, the reaction was quenched by 1 N HCl (1 mL) and stirred for 5 minutes. EtOAc was added and the reaction was washed once with saturated NaHCO₃, dried over MgSO₄ and evaporated. The product was recrystallized in MeOH and water to afford the product as a white solid (68 mg, 0.18 mmol, 64% yield). MP=145.1-146.5° C. (145.8° C.)¹H NMR (300 MHz, DMSO-d₆) δ 8.25 (s, 1H), 7.86-7.81 (m, 3H) 7.65 (s, 1H), 7.48-7.40 (m, 2H), 7.37 (s, 1H), 7.31 (d, J=9.0 Hz, 2H), 6.78 (d, J=8.6 Hz, 2H), 4.06 (d, J=13.1 Hz, 2H), 3.67 (s, 3H), 2.76-2.60 (m, 4H), 1.86-1.73 (b, 1H), 1.58 (d, J=12.6 Hz, 2H), 1.13 (q, J=12.0 Hz, 2H).

Example 26. B-9. N-(4-methoxyphenyl)-4-(3-((5-(trifluoromethyl)pyridin-2-yl)oxy)benzyl) piperidine-1-carboxamide

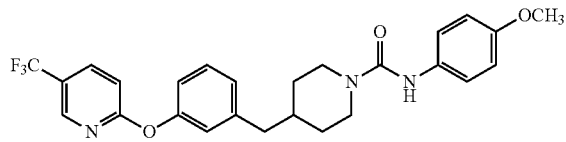 [SMILES: COc1ccc(NC(=O)N2CCC(Cc3cccc(Oc4ccc(C(F)(F)F)cn4)c3)CC2)cc1]

To a solution of 2-(3-(piperidin-4-ylmethyl)phenoxy)-5-(trifluoromethyl)pyridine (Ahn et al. (2009) *Chem. Biol.* 16:411, 137 mg, 0.41 mmol) dissolved in THF (10 mL) was added 4-trifluoromethoxyphenyl isocyanate (61 mg, 0.41 mmol). The solution was allowed to stir overnight and the reaction was quenched by addition of 1 N HCl (5 mL). The reaction was neutralized by adding to sat. $NaHCO_3$, the product was extracted with EtOAc, dried over $NaSO_4$ and evaporated. The resulting solid was sonicated in ether (20 mL) for 5 minutes and filtered to give the product as a white solid (155 mg, 0.32 mmol, 76%). MP=155.2-158.3° C. (156.7° C.).$^1$H NMR (300 MHz, DMSO-$d_6$) δ 8.58 (s, 1H), 8.26 (s, 1H), 8.22 (dd, J=8.9, 2.4 Hz, 1H), 7.40-7.31 (m, 3H) 7.21 (d, J=8.7 Hz, 1H), 7.10 (d, J=7.7 Hz, 1H), 7.06-7.01 (m, 2H), 6.80 (d, J=9.1 Hz, 2H), 4.08 (d, J=13.2 Hz, 2H), 3.70 (s, 3H), 2.70 (t, J=11.8 Hz, 2H), 2.56 (d, J=6.9 Hz, 2H), 1.80-169 (b, 1H), 1.59 (d, J=12.9 Hz, 2H), 1.20-1.03 (m, 2H).

Example 27. B-10. N-(4-methoxyphenyl)-4-(4-phenylthiazol-2-yl)piperidine-1-carboxamide

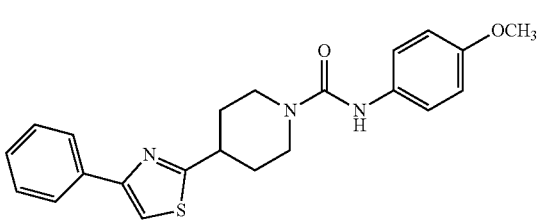 [SMILES: COc1ccc(NC(=O)N2CCC(c3nc(-c4ccccc4)cs3)CC2)cc1]

4-phenyl-2-(piperidin-4-yl)thiazole (Kono et al. (2013) *Bioorg. Med. Chem.* 21:28, 36 mg, 0.15 mmol) and 4-methoxyphenylisocyanate (23 mg, 0.15 mmol) were added to THF (5 mL) and stirred overnight. The reaction was quenched by the addition of 1 N HCl and saturated $NaHCO_3$ and EtOAc were added to the solution. The organic layer was collected and washed 2 additional times with sat. $NaHCO_3$, dried over MgSO4 and evaporated. The isolated product crystallized on addition of ice cold EtOAc, filtered and washed with cold 1:1 EtOAc:Hexane. The resulting product was isolated as white crystals (25 mg, 0.06 mmol, 42% yield). MP=139.8-146.1° C. (143.8° C.)$^1$H NMR (300 MHz, DMSO-$d_6$) δ 8.37 (s, 1H), 7.98 (s, 1H), 7.93 (d, J=7.0 Hz, 2H), 7.42 (t, J=7.5 Hz, 2H), 7.38-7.27 (m, 3H), 6.80 (d, J=9.0 Hz, 2H), 4.18 (d, J=13.3 Hz, 2H), 3.68 (s, 3H), 2.96 (t, J=12.7 Hz, 2H), 2.10 (d, J=13.3 Hz, 2H), 1.66 (qd, J=12.2, 4.0 Hz, 2H).

Example 28. B-11. N-(4-(trifluoromethoxy)phenyl)-4-(3-((5-(trifluoromethyl)pyridin-2-yl)oxy)benzyl) piperidine-1-carboxamide

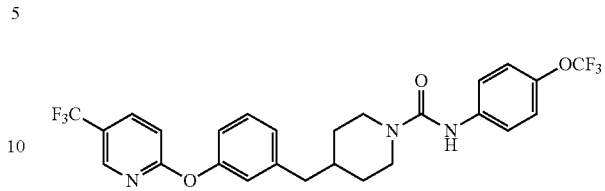

2-(3-(piperidin-4-ylmethyl)phenoxy)-5-(trifluoromethyl)pyridine (275 mg, 0.82 mmol) and 4-trifluoromethoxyphenyl isocyanate (162 mg, 0.80 mmol) were dissolved in THF (15 mL). The reaction was stirred overnight and quenched by addition of 1 N HCl (1 mL). EtOAc was added and the organic layer was extracted once with saturated $NaHCO_3$, dried over $MgSO_4$ and evaporated. The mixture was purified by column chromatography with 1:1 Hex:EtOAc to afford the product as a slightly peach colored solid (274 mg, 0.51 mmol, 64%). MP=97.4-99.7 (98.6° C.). $^1$H NMR (300 MHz, DMSO-$d_6$) δ 8.63 (s, 1H), 8.58 (d, J=2.5 Hz, 1H), 8.23 (dd, J=8.7, 2.6 Hz, 1H), 7.55 (d, J=9.1 Hz, 1H), 7.37 (dd, J=8.8, 7.5 Hz, 1H), 7.21 (d, J=8.7 Hz, 3H), 7.10 (d, J=7.9 Hz, 1H), 7.03 (dd, J=4.3, 2.0 Hz, 2H), 4.10 (d, J=13.2 Hz, 2H), 2.74 (td, J=12.9, 2.5 Hz, 2H), 2.57 (d, J=7.0 Hz, 2H), 1.88-1.67 (m, 1H), 1.67-1.52 (m, 2H), 1.14 (td, J=12.2, 3.8 Hz, 2H).

Example 29. B-12. N-(4-chlorophenyl)-4-(3-((5-(trifluoromethyl)pyridin-2-yl)oxy)benzyl) piperidine-1-carboxamide

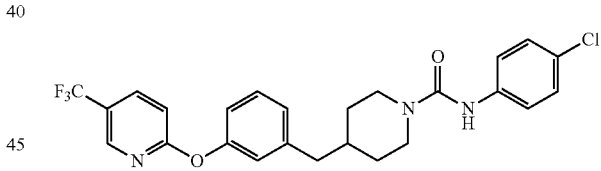

2-(3-(piperidin-4-ylmethyl)phenoxy)-5-(trifluoromethyl)pyridine (113 mg, 0.36 mmol) and 4-chlorophenyl isocyanate (56 mg, 0.37 mmol) were dissolved in THF (10 mL). After stirring overnight, the reaction was quenched with 1 N HCl (1 mL) and stirred for 10 minutes. EtOAc was added to the reaction mixture and the organic mixture was extracted 2× with saturated $NaHCO_3$, dried with MgSO4 and evaporated. MeOH (20 mL) was added to the resulting solid and the mixture was sonicated for 5 minutes. The filtered white solid appeared as a single spot on TLC and was used as is (74 mg, 0.15 mmol, 42%). MP=161.1-166.2° C. (165.1° C.)$^1$H NMR (300 MHz, DMSO-$d_6$) δ 8.63-8.53 (m, 2H), 8.22 (dd, J=8.8, 2.6 Hz, 1H), 7.48 (d, J=8.9 Hz, 2H), 7.37 (dd, J=8.7, 7.6 Hz, 1H), 7.29-7.18 (m, 3H), 7.13-7.06 (m, 1H), 7.05-6.99 (m, 2H), 4.08 (d, J=12.7 Hz, 3H), 2.73 (t, J=12.5 Hz, 3H), 2.56 (d, J=7.0 Hz, 3H), 1.82-1.67 (m, 1H), 1.60 (d, J=13.0 Hz, 2H), 1.16-1.02 (m, 2H).

Example 30. B-13. N-(4-(trifluoromethyl)phenyl)-4-(3-((5-(trifluoromethyl)pyridin-2-yl)oxy)benzyl)piperidine-1-carboxamide

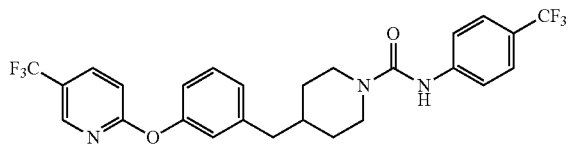 [SMILES: O=C(Nc1ccc(C(F)(F)F)cc1)N1CCC(Cc2cccc(Oc3ccc(C(F)(F)F)cn3)c2)CC1]

2-(3-(piperidin-4-ylmethyl)phenoxy)-5-(trifluoromethyl)pyridine (309 mg, 0.91 mmol) and 4-trifluoromethylphenyl isocyanate (175 mg, 0.94 mmol) were dissolved in THF (10 mL). After stirring overnight, the reaction was quenched with 0.1 N HCl (80 mL) and stirred for 10 minutes. EtOAc (80 mL) was added to the reaction mixture and the organic mixture was separated, dried with $Na_2CO_3$ and evaporated. The crude product was separated by silica column chromatography using 7:3 Hexane:EtOAc. The final product was recrystallized as a white solid in $H_2O$/MeOH (220 mg, 0.41 mmol, 45% yield). MP=50.5-55.5° C. (51.5° C.) $^1$H NMR (300 MHz, DMSO-$d_6$) δ 8.83 (s, 1H), 8.57 (s, 1H), 8.22 (dd, J=8.7, 2.6 Hz, 1H), 7.67 (d, J=8.5 Hz, 2H), 7.55 (d, J=8.6 Hz, 2H), 7.37 (dd, J=8.7, 7.5 Hz, 1H), 7.20 (d, J=8.7 Hz, 1H), 7.10 (d, J=7.5 Hz, 1H), 7.07-6.98 (m, 2H), 4.10 (d, J=13.3 Hz, 2H), 2.75 (t, J=12.5 Hz, 2H), 2.57 (d, J=6.9 Hz, 2H), 1.84-1.68 (m, 1H), 1.61 (d, J=11.9 Hz, 2H), 1.12 (q, J=12.1, 10.8 Hz, 2H).

Example 31. B-14. N-(5-(trifluoromethyl)pyridin-2-yl)-4-(3-((5-(trifluoromethyl)pyridin-2-yl)oxy)benzyl)piperidine-1-carboxamide

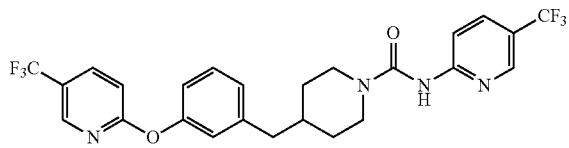 [SMILES: O=C(Nc1ccc(C(F)(F)F)cn1)N1CCC(Cc2cccc(Oc3ccc(C(F)(F)F)cn3)c2)CC1]

Phenyl (5-(trifluoromethyl)pyridin-2-yl)carbamate

Phenyl chloroformate (620 mg, 3.96 mmol) was added to a solution of 5-(trifluoromethyl)pyridin-2-amine (615 mg, 3.79 mmol) and pyridine (323 mg, 4.08 mmol) in ACN (50 mL) at 0° C. After stirring the solution overnight at room temperature, the reaction was quenched with $H_2O$. The resulting precipitate was filtered, dried and used without further purification. The product was a white solid (905 mg, 3.21 mmol, 84% yield).

N-(5-(trifluoromethyl)pyridin-2-yl)-4-(3-((5-(trifluoromethyl)pyridin-2-yl)oxy)benzyl)piperidine-1-carboxamide 2-(3-(piperidin-4-ylmethyl)phenoxy)-5-(trifluoromethyl)pyridine (319 mg, 0.95 mmol), phenyl pyridazin-3-ylcarbamate (309 mg, 1.10 mmol) and N,N'-diisopropylethylamine (145 mg, 1.12 mmol) were dissolved in DMSO (15 mL). After stirring overnight at 55° C., the reaction was quenched with water and stirred for 5 minutes. The crude mixture was extracted with EtOAc, dried with $Na_2CO_3$ and evaporated. The product was purified silica column chromatography using 8:2 Hexanes:EtOAc. The final product was recrystallized as a beige solid in $H_2O$/MeOH (229 mg, 0.44 mmol, 46% yield). MP=107.6-111.6° C. (109.5° C.) $^1$H NMR (300 MHz, DMSO-$d_6$) δ 9.04 (s, 1H), 8.57-8.53 (m, 1H), 8.21 (dd, J=8.8, 2.6 Hz, 1H), 8.11 (dd, J=8.6, 2.5 Hz, 1H), 7.73 (d, J=8.7 Hz, 1H), 7.35 (dd, J=8.8, 7.6 Hz, 1H), 7.19 (d, J=8.7 Hz, 1H), 7.12-7.05 (m, 1H), 7.06-6.97 (m, 2H), 4.10 (d, J=13.2 Hz, 2H), 2.77 (t, J=12.6 Hz, 2H), 2.55 (d, J=7.0 Hz, 2H), 1.88-1.67 (m, 1H), 1.61 (d, J=13.0 Hz, 2H), 1.21-1.01 (m, 2H).

Example 32. B-15. 4-(3-((5-(trifluoromethyl)pyridin-2-yl)oxy)benzyl)-N-(6-(trifluoromethyl)pyridin-3-yl)piperidine-1-carboxamide

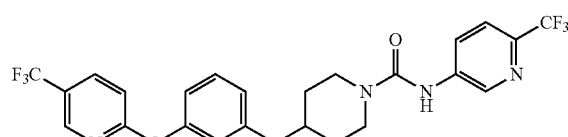

Phenyl (6-(trifluoromethyl)pyridin-3-yl)carbamate

Phenyl chloroformate (356 mg, 2.27 mmol) was added to a solution of 6-(trifluoromethyl)pyridin-3-amine (312 mg, 1.92 mmol) and pyridine (164 mg, 2.07 mmol) in ACN (10 mL) at 0° C. After stirring the solution overnight at room temperature, the reaction was quenched with $H_2O$. The resulting precipitate was filtered, dried and used without further purification. The product was a white solid (478 mg, 1.70 mmol, 88% yield).

4-(3-((5-(trifluoromethyl)pyridin-2-yl)oxy)benzyl)-N-(6-(trifluoromethyl)pyridin-3-yl)piperidine-1-carboxamide (B-15)

2-(3-(piperidin-4-ylmethyl)phenoxy)-5-(trifluoromethyl)pyridine (292 mg, 0.87 mmol), phenyl pyridazin-3-ylcarbamate (284 mg, 1.01 mmol) and N,N'-diisopropylethylamine (145 mg, 1.12 mmol) were dissolved in DMSO (15 mL). After stirring overnight at 55° C., the reaction was quenched with water and stirred for 5 minutes. The crude mixture was extracted with EtOAc, dried with $Na_2CO_3$ and evaporated. The product was purified silica column chromatography using 8:2 Hexanes:EtOAc. The final product was recrystallized as a beige solid in $H_2O$/MeOH (216 mg, 0.41 mmol, 47% yield). MP=88.7-91.2° C. (89.7° C.) $^1$H NMR (300 MHz, DMSO-$d_6$) δ 9.68 (s, 1H), 8.58 (d, J=2.8 Hz, 2H), 8.24 (dd, J=8.8, 2.6 Hz, 1H), 8.04 (dd, J=9.0, 2.5 Hz, 1H), 7.95 (d, J=9.0 Hz, 1H), 7.44-7.32 (m, 1H), 7.22 (d, J=8.7 Hz, 1H), 7.11 (d, J=7.6 Hz, 1H), 7.07-7.00 (m, 2H), 4.15 (d, J=13.2 Hz, 2H), 2.78 (t, J=12.5 Hz, 2H), 2.57 (d, J=7.1 Hz, 2H), 1.91-1.68 (m, 1H), 1.61 (d, J=13.0 Hz, 2H), 1.28-1.04 (m, 2H).

Example 33. B-16. N-(pyridazin-3-yl)-4-(3-((5-(trifluoromethyl)pyridin-2-yl)oxy)benzyl)piperidine-1-carboxamide

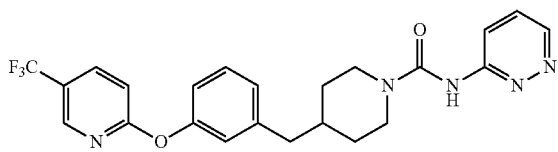 [SMILES: O=C(Nc1cccnn1)N1CCC(Cc2cccc(Oc3ccc(C(F)(F)F)cn3)c2)CC1]

Phenyl pyridazin-3-ylcarbamate

Phenyl chloroformate (365 mg, 2.33 mmol) was added to a solution of pyridazin-3-amine (178 mg, 1.87 mmol) and pyridine (185 mg, 2.34 mmol) in ACN (10 mL) at 0° C. After stirring the solution overnight at room temperature, the reaction was quenched with H$_2$O (50 mL). The product was extracted with EtOAc (50 mL), dried with Na$_2$SO$_4$ and evaporated to 5 mL. The beige solid precipitated and was filtered to give the product (299 mg, 1.39 mmol, 74% yield).

N-(pyridazin-3-yl)-4-(3-((5-(trifluoromethyl)pyridin-2-yl)oxy)benzyl)piperidine-1-carboxamide (B-16)

2-(3-(piperidin-4-ylmethyl)phenoxy)-5-(trifluoromethyl)pyridine (141 mg, 0.42 mmol), phenyl pyridazin-3-ylcarbamate (88 mg, 0.41 mmol) and N,N'-diisopropylethylamine (107 mg, 0.83 mmol) were dissolved in DMSO (10 mL). After stirring overnight at 55° C., the reaction was quenched with 1N HCl and stirred for 5 minutes. The crude mixture was extracted with EtOAc, dried with Na$_2$CO$_3$ and evaporated. The product was purified silica column chromatography using 19:1 DCM:MeOH. The final product was recrystallized as a beige solid in H$_2$O/MeOH (65 mg, 0.14 mmol, 35% yield). MP=99.8-104.2° C. (101.6° C.) $^1$H NMR (300 MHz, DMSO-d$_6$) δ 9.76 (s, 1H), 8.83 (d, J=4.6 Hz, 1H), 8.59 (s, 1H), 8.24 (dd, J=8.7, 2.6 Hz, 1H), 7.98 (dd, J=8.9, 1.4 Hz, 1H), 7.56 (dd, J=9.1, 4.6 Hz, 1H), 7.44-7.33 (m, 1H), 7.22 (d, J=8.7 Hz, 1H), 7.11 (d, J=8.1 Hz, 1H), 7.04 (t, J=2.9 Hz, 2H), 4.18 (d, J=13.3 Hz, 2H), 2.79 (t, J=12.7 Hz, 2H), 2.58 (d, J=7.1 Hz, 2H), 1.88-1.70 (m, 1H), 1.62 (d, J=13.0 Hz, 2H), 1.28-1.05 (m, 2H).

Example 34. B-17. N-(3,4-dimethylisoxazol-5-yl)-4-(3-((5-(trifluoromethyl)pyridin-2-yl)oxy)benzyl)piperidine-1-carboxamide

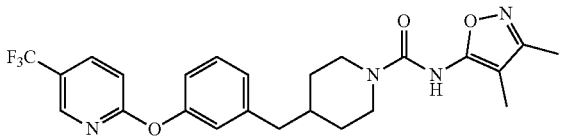 [SMILES: Cc1noc(NC(=O)N2CCC(Cc3cccc(Oc4ccc(C(F)(F)F)cn4)c3)CC2)c1C]

Phenyl (3,4-dimethylisoxazol-5-yl)carbamate

Phenyl chloroformate (280 mg, 1.79 mmol) was added to a solution of 5-amino-3,4-dimethylisoxazole (159 mg, 1.42 mmol) and pyridine (141 mg, 1.78 mmol) in ACN (10 mL) at 0° C. After stirring the solution overnight at room temperature, the reaction was quenched with H$_2$O. The product was extracted with EtOAc (50 mL), dried with Na$_2$SO$_4$ and evaporated to afford a brown liquid that solidified under vacuum overnight. The impure product was used without further purification (390 mg, 1.68 mmol, 120% yield).

N-(3,4-dimethylisoxazol-5-yl)-4-(3-((5-(trifluoromethyl)pyridin-2-yl)oxy)benzyl)piperidine-1-carboxamide (B-17)

2-(3-(piperidin-4-ylmethyl)phenoxy)-5-(trifluoromethyl)pyridine (138 mg, 0.41 mmol), phenyl (3,4-dimethylisoxazol-5-yl)carbamate (114 mg, 0.49 mmol) and N,N'-diisopropylethylamine (113 mg, 0.88 mmol) were dissolved in DMSO (10 mL). After stirring overnight at 55° C., the reaction was quenched 1N HCl and stirred for 5 minutes. The crude mixture was extracted with EtOAc, dried with Na$_2$CO$_3$ and evaporated. The product was purified silica column chromatography using 19:1 DCM:MeOH. The final product was recrystallized as a white solid in H$_2$O/MeOH (102 mg, 0.22 mmol, 52% yield). MP=41.8-53.0° C. (45.5° C.). $^1$H NMR (300 MHz, DMSO-d$_6$) δ 9.01 (s, 1H), 8.56 (d, J=2.6 Hz, 1H), 8.21 (dd, J=8.4, 2.6 Hz, 1H), 7.35 (t, J=8.1 Hz, 1H), 7.19 (d, J=8.7 Hz, 1H), 7.08 (d, J=7.5 Hz, 1H), 7.05-6.97 (m, 1H), 6.73 (d, J=7.6 Hz, 1H), 4.07-3.89 (m, 2H), 2.73 (t, J=12.4 Hz, 2H), 2.55 (d, J=7.0 Hz, 2H), 2.09 (s, 3H), 1.70 (s, 4H), 1.57 (d, J=12.9 Hz, 2H), 1.20-1.00 (m, 2H).

Example 35. B-18. N-(2-fluoro-4-(trifluoromethyl)phenyl)-4-(3-((5-(trifluoromethyl)pyridin-2-yl)oxy)benzyl)piperidine-1-carboxamide

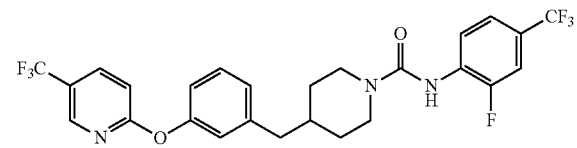 [SMILES: O=C(Nc1ccc(C(F)(F)F)cc1F)N1CCC(Cc2cccc(Oc3ccc(C(F)(F)F)cn3)c2)CC1]

Phenyl (2-fluoro-4-(trifluoromethyl)phenyl)carbamate

Phenyl chloroformate (215 mg, 1.34 mmol) was added to a solution of 2-fluoro-4-(trifluoromethyl)aniline (207 mg, 1.16 mmol) and pyridine (101 mg, 1.28 mmol) in ACN (10 mL) at 0° C. After stirring the solution overnight at room temperature, the reaction was quenched with H$_2$O. The resulting precipitate was filtered, dried and used without further purification. The product was a white solid (293 mg, mmol, yield). $^1$H NMR (300 MHz, DMSO-d$_6$) δ 10.40 (s, 1H), 8.04 (t, J=8.2 Hz, 1H), 7.76 (d, J=10.9 Hz, 1H), 7.61 (d, J=9.3 Hz, 1H), 7.45 (t, J=7.8 Hz, 2H), 7.32-7.21 (m, 3H).

N-(2-fluoro-4-(trifluoromethyl)phenyl)-4-(3-((5-(trifluoromethyl)pyridin-2-yl)oxy)benzyl)piperidine-1-carboxamide (B-18)

2-(3-(piperidin-4-ylmethyl)phenoxy)-5-(trifluoromethyl)pyridine (238 mg, 0.71 mmol), phenyl (2-fluoro-4-(trifluoromethyl)phenyl)carbamate (218 mg, 0.73 mmol) and N,N'-diisopropylethylamine (104 mg, 0.81 mmol) were dissolved in DMSO (15 mL). After stirring overnight at 55° C., the reaction was quenched with water and stirred for 5 minutes. The crude mixture was extracted with EtOAc, dried with Na$_2$CO$_3$ and evaporated. The product was purified silica column chromatography using 8:2 Hexane:EtOAc. The final product was recrystallized as a white solid in H$_2$O/MeOH (122 mg, 0.23 mmol, 32% yield). MP=106.0=108.5° C. (107.1° C.)$^1$H NMR (300 MHz, DMSO-d$_6$) δ 8.57 (d, J=8.5 Hz, 1H), 8.24 (d, J=9.2 Hz, 1H), 7.74 (t, J=8.2 Hz, 1H), 7.63 (d, J=11.0 Hz, 1H), 7.49 (d, J=8.5 Hz, 1H), 7.38 (t, J=8.1 Hz, 1H), 7.22 (d, J=8.7 Hz, 1H), 7.12 (d, J=7.6 Hz, 1H), 7.05 (s, 2H), 4.08 (d, J=13.2 Hz, 2H), 2.79 (t, J=12.7 Hz, 2H), 2.58 (d, J=7.2 Hz, 2H), 1.78 (s, 1H), 1.63 (d, J=12.2 Hz, 2H), 1.29-1.06 (m, 2H).

Example 36. Screening of sEH Inhibitors for FAAH Potentcy

A crude preparation of recombinant FAAH enzyme was derived from baculovirus with the fluorescent-based substrate, octamide 4-methoxypyridine (OMP). Approximately 1700 compounds designed to inhibit sEH were tested with the FFAH preparation. Results shown in FIG. 1 were used to determine that only 38 of the tested compounds inhibited at least 75% of the FAAH enzyme activity at 10 μM. Of these 38, trans-4-{4-[3-(4-trifluoromethoxyphenyl)-ureido] cyclohexyloxy}benzoic acid (t-TUCB) had the highest potency, with an IC$_{50}$ value of 140 nM. Although t-TUCB appears to have potency on FAAH, its relative inhibitory effect is low when compared to that of other molecules not considered to be dual sEH/FAAH inhibitors.

Example 37. Development of Dual Inhibitors of sEH and FAAH Through Modification of t-TUCB To improve inhibition potency relative to FAAH, various portions of the t-TUCB molecule were modified to identify potential FAAH pharmacophores. The 4-trifluoromethoxy group on t-TUCB was modified to the unsubstituted ring (A-3), 4-fluorophenyl (A-2) or 4-chlorophenyl (A-26). Potency on both sEH and FAAH increased as the size and hydrophobicity of the para position substituent increased, with 4-trifluoromethoxy being the most potent on both enzymes. Substituting the aromatic ring for a cyclohexane (A-3) or adamantane (A-4) resulted in a complete loss in activity against FAAH. Results are summarized in Table 1 below.

TABLE 1

Modification of the 4-trifluoromethoxy group of t-TUCB

|   | R$^2$ | —N(R$^3$)—L$^1$— | Stereochemistry | IC$_{50}$ (nM) hsEH | IC$_{50}$ (nM) hFAAH |
|---|---|---|---|---|---|
| t-TUCB | F$_3$CO-phenyl | NH-cyclohexyl | trans | 0.8 | 140 |
| A-1 | phenyl | NH-cyclohexyl | trans | 30 | 9,200 |
| A-2 | F-phenyl | NH-cyclohexyl | trans | 18 | 4,600 |
| A-26 | Cl-phenyl | NH-cyclohexyl | trans | 7 | 680 |

TABLE 1-continued

Modification of the 4-trifluoromethoxy group of t-TUCB

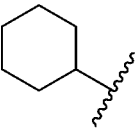 [SMILES: *C1CCCCC1]

| | R² | —N(R³)—L¹— | Stereochemistry | IC₅₀ (nM) hsEH | IC₅₀ (nM) hFAAH |
|---|---|---|---|---|---|
| A-3 | 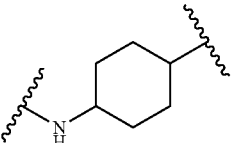 | 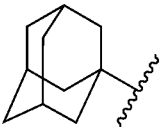 | trans | 6 | >1,000 |
| A-4 | 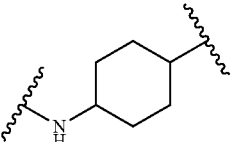 | 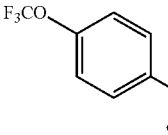 | trans | 3 | >10,000 |
| A-10 | F₃CO— 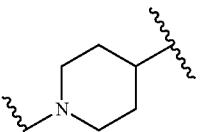 |  | | 8 | 1,800 |

Next, the center portion of the molecule was modified to further investigate the specificity of t-TUCB on FAAH. Switching the cyclohexane linker to a cis conformation (A-5) resulted in a 20-fold loss of potency while removing the ring and replacing it with a butane chain (A-6) resulted in a completely inactive compound. While this suggests the compound must fit a relatively specific conformation in the active site to be active, we found the aromatic linker had essentially the same potency on FAAH (A-7). Although many potent urea-based FAAH inhibitors have a piperidine as the carbamoylating nitrogen, the modification to piperidine here reduced potency 13-fold. Results are summarized in Table 2 below.

TABLE 2

Modification of the central portion of t-TUCB

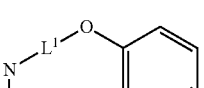

| | R² | —N(R³)—L¹— | Stereochemistry | IC₅₀ (nM) hsEH | IC₅₀ (nM) hFAAH |
|---|---|---|---|---|---|
| t-TUCB | F₃CO— | | trans | 0.8 | 140 |

TABLE 2-continued

Modification of the central portion of t-TUCB

| | R² | —N(R³)—L¹— | Stereochemistry | IC₅₀ (nM) hsEH | IC₅₀ (nM) hFAAH |
|---|---|---|---|---|---|
| A-5 | F₃CO-phenyl | cyclohexyl-NH- | cis | 2 | 2,800 |
| A-6 | F₃CO-phenyl | -NH-(CH₂)₄- | | 15 | >10,000 |
| A-7 | F₃CO-phenyl | -NH-phenyl- | | 7 | 170 |

Since none of the modifications at this point improved potency towards FAAH, we focused on the benzoic acid portion of the molecule as shown in Table 3. To determine the importance of the terminal acid, the corresponding aldehyde (A-20) and alcohol (A-24) in addition to the amide (A-19) and nitrile (A-11) were tested. While the amide had slightly improved potency, the more reduced forms of the acid (A-20 and A-24) and amide (A-11) had substantially less activity on FAAH. Converting the benzoic acid to a phenol (A-21) increased potency while the anisole (A-22) was completely inactive. Since the amide and acid appeared to be active, the amide bioisostere oxadiazole (A-25) was tested and had 38-fold less potency than the initial compound.

TABLE 3

Modification of the benzoic acid portion of t-TUCB

| | R¹ | IC₅₀ (nM) hsEH | IC₅₀ (nM) hFAAH |
|---|---|---|---|
| t-TUCB | -C(O)OH | 0.8 | 140 |

TABLE 3-continued

Modification of the benzoic acid portion of t-TUCB

| | R¹ | IC₅₀ (nM) hsEH | IC₅₀ (nM) hFAAH |
|---|---|---|---|
| A-11 | -CN | 5 | >10,000 |
| A-19 | -C(O)NH₂ | 2 | 70 |
| A-20 | -C(O)H | 4 | 1,100 |
| A-24 | -CH₂OH | 3 | 5,800 |

TABLE 3-continued

Modification of the benzoic acid portion of t-TUCB

F₃CO–⟨benzene⟩–NH–C(O)–NH–⟨cyclohexane⟩–O–⟨benzene⟩–R¹

| | | IC₅₀ (nM) | |
|---|---|---|---|
| | R¹ | hsEH | hFAAH |
| A-21 | —OH | 2 | 120 |
| A-22 | —OCH₃ | 3 | >10,000 |
| A-25 | 2-methyl-1,3,4-oxadiazol-5-yl | 4 | 5,300 |

Since the substrates for FAAH tend to be relatively hydrophobic lipids, we speculated that conversion of the acid and primary amide to the corresponding esters or substituted amides would result in improved potency. The methyl ester (A-12) had 4-fold improved potency relative to the acid. Improving the bulk of the ester with an isopropyl group (A-13) results in a 11-fold loss in potency relative to the methyl ester. However, the similar potency of the benzyl ester (A-14) to the methyl ester demonstrates the bulk but not the size affects potency. Reversing the orientation of the ester (A-23) reduces the potency 3.4-fold. Relative to the primary amide, the methyl (A-18), ethanol (A-15) and glycyl (A-16) amides were all slightly less potent; however, the benzyl amide (A-27) was substantially less potent (16-fold). Generating the methyl ester of the glycyl amide (A-17) increased the potency 4-fold compared to the corresponding acid.

TABLE 4

Potency of ester and amide conjugates of t-TUCB

F₃CO–⟨benzene⟩–NH–C(O)–NH–⟨cyclohexane⟩–O–⟨benzene⟩–R¹

| | | IC₅₀ (nM) | |
|---|---|---|---|
| | R¹ | hsEH | hFAAH |
| t-TUCB | —C(O)OH | 0.8 | 140 |
| A-12 | —C(O)OCH₃ | 7 | 35 |
| A-13 | —C(O)O-iPr | 5 | 400 |
| A-14 | —C(O)O-CH₂-phenyl | 3 | 24 |
| A-23 | —O-C(O)-CH₃ | 4 | 120 |
| A-18 | —C(O)NH-CH₃ | 2 | 170 |
| A-15 | —C(O)NH-CH₂CH₂OH | 2 | 100 |
| A-16 | —C(O)NH-CH₂-C(O)OH | 2 | 130 |
| A-17 | —C(O)NH-CH₂-C(O)OCH₃ | 3 | 30 |
| A-27 | —C(O)NH-CH₂-phenyl | 5 | 1,100 |

Example 38. Biochemistry of A-14 and A-21 Inhibition Mechanisms

Figure 2:
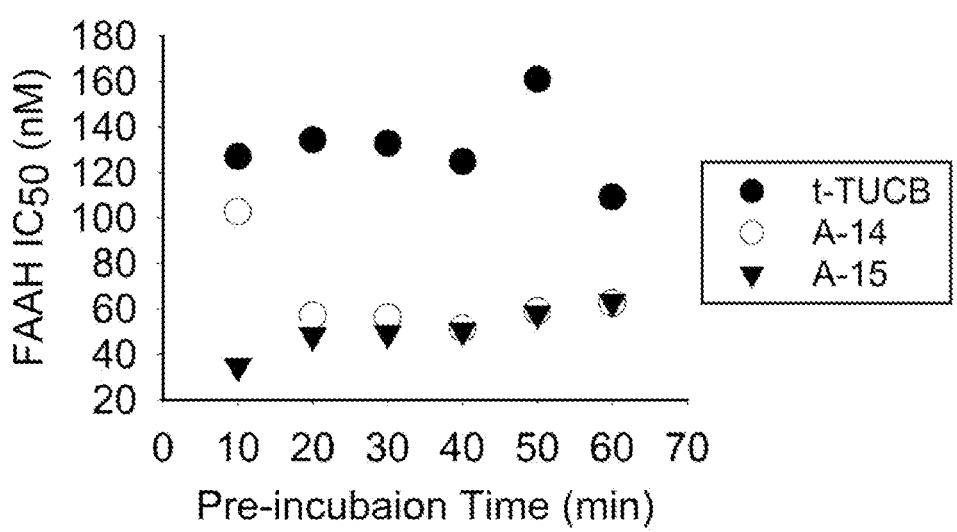
FIG. 2 shows FAAH inhibition potencies of t-TUCB, A-14, and A-21 compounds at different concentrations and pre-incubation times.
Figure 3:
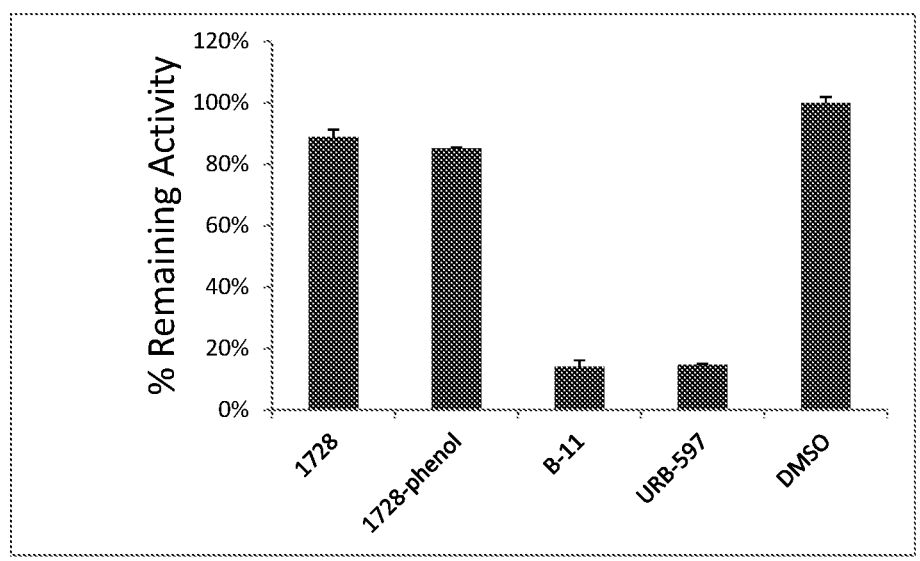
FIG. 3 shows dilution of FAAH enzyme with inhibitor recovers activity after incubation of t-TUCB and A-21 and does not recover activity after incubation of B-11.

Biochemical analyses were performed on the t-TUCB compound and the optimized structures, A-14 and A-21. Results in FIG. 2 show that all three compounds had little change in potency when comparing the IC₅₀ over a 1 hour time-course, indicating a reversible mechanism of inhibition. Reversibility was tested using a dilution-based assay. t-TUCB was incubated with enzyme for 30 minutes at concentration of 10 uM and diluted 1000-fold for a final inhibitor concentration of 10 nM. Comparing the $IC_{50}$ of t-TUCB on FAAH at varying substrate concentrations demonstrates that the potency of t-TUCB is dependent on the concentration of substrate, indicating a competitive mode of inhibition.

Example 39. Selectivity of A-14 and A-21

Generally, pharmacophores for FAAH inhibitors, urea and non-urea based, interact by either carbamoylating or forming transition-state mimics with the catalytic serine residue. However, since a large number of hydrolases utilize a similar catalytic serine residue, many FAAH inhibitors have suffered from poor selectivity. Therefore, the potency of t-TUCB, A-14 and A-21 on several other serine hydrolases was tested. Included in this panel were carboxylesterases, hydrolases involved in xenobiotic detoxification, and paraoxonases and esterases involved in the regulation of artherosclerosis. As is shown in Table 5 below, none of these serine hydrolases were inhibited by t-TUCB, A-14, or A-21.

TABLE 5

Selectivity of A-14 and A-15 against other serine hydrolases.

| | $IC_{50}$ (nM) | | |
|---|---|---|---|
| Enzyme | 1728 | A-14 | A-21 |
| FAAH | 140 | 24 | 120 |
| sEH | 0.8 | 3 | 2 |
| MAGL | >10,000 | >10,000 | >10,000 |
| hCE1 | >10,000 | >10,000 | >10,000 |
| hCE2 | >10,000 | >10,000 | >10,000 |
| PON1 | >10,000 | >10,000 | >10,000 |
| PON2 | >10,000 | >10,000 | >10,000 |
| PON3 | >10,000 | >10,000 | >10,000 |
| AADAC | >10,000 | >10,000 | 5,400 |

Example 40. Potency in Multiple Species

Extensive studies have used t-TUCB to investigate the role of sEH in multiple animal models. The $IC_{50}$ on FAAH in various species was determined using brain microsome preparations to test whether potency towards FAAH may account for additional efficacy in these animal models. To prove FAAH accounts for the majority of OMP hydrolysis in brain microsomes, we additionally measured the $IC_{50}$ of two well characterized FAAH inhibitors, PF-3845 and URB-597. These two inhibitors are structurally distinct and have excellent selectivity in rat brain microsomes. Since both inhibitors blocked >80% of the activity in the microsomes of other species, the measured $IC_{50}$ values should approximately represent the real $IC_{50}$ of inhibitors in other species. From results shown in both t-TUCB and A-14 are over 10-fold less potent in all other species tested. By comparison, A-21 had comparable $IC_{50}$ values in all species except rats, where A-21 was 5-fold less potent on FAAH.

TABLE 6

Comparison of potencies on FAAH in multiple species

| | | $IC_{50}$ (nM) | | | | |
|---|---|---|---|---|---|---|
| Enzyme | Species | 1728 | A-14 | A-21 | PF-3845 | URB597 |
| FAAH | Human | 140 | 24 | 120 | 0.4 | 40 |
| | Mouse | >1,000 | 440 | 89 | 4.0 | 11 |
| | Rat | >1,000 | >1,000 | 780 | 4.4 | 12 |

TABLE 6-continued

Comparison of potencies on FAAH in multiple species

| | | $IC_{50}$ (nM) | | | | |
|---|---|---|---|---|---|---|
| Enzyme | Species | 1728 | A-14 | A-21 | PF-3845 | URB597 |
| | Cat | >1,000 | >1,000 | 130 | <0.1 | 12 |
| | Dog | >1,000 | >1,000 | 220 | 0.4 | 22 |
| sEH | Human | 0.8 | 3 | 2 | — | — |
| | Mouse | 5.7 | 2.1 | 0.4 | — | — |
| | Rat | 54 | 1.6 | 1.0 | — | — |

Example 41. Development of Dual Inhibitors of sEH and FAAH Through Modification of PF-750

PF-750 is a commercially available FAAH inhibitor having low but biologically relevant additional potency towards sEH. A series of new compounds were synthesized where the 3-(piperidin-4-ylmethyl)quinolone carbamoylating group from PF-750 was kept the same and the aromatic leaving group was modified. The unsubstituted ring was modified to add fluorine (B-1) and chlorine (B-2) in the 4 position. This increased activity towards sEH 7- and 30-fold, respectively, while decreasing activity towards FAAH 4- and 3-fold. Addition of a fluorine to the 2 position (B-3) increased potency 2.5-fold towards FAAH while having modest effect on sEH. Substitution to the 4-trifluoromethoxy (B-4) improved sEH potency 80-fold while also reducing FAAH potency by 20.5-fold. In comparison, the 4-methoxy (B-5) had a 4-fold increase in potency towards sEH while having a modest effect on FAAH. Although conversion of the phenyl ring to the 3-pyridine (B-6) did decrease sEH potency, it did not have much effect towards FAAH. A summary of observed results is given in Table 7 below.

TABLE 7

Modification of the Aryl Leaving Group from PF-750

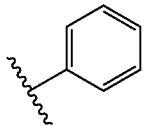

| | —$L^1$—$R^1$ | hsEH $IC_{50}$ (nM) | hFAAH $IC_{50}$ (nM) |
|---|---|---|---|
| PF-750 | 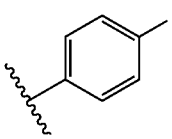 | 640 ± 200 | 19 |
| B-1 | | 94 ± 42 | 88 |
| B-2 | | 20 ± 4 | 62 |

TABLE 7-continued

Modification of the Aryl Leaving Group from PF-750

| —L¹—R¹ | | hsEH IC$_{50}$ (nM) | hFAAH IC$_{50}$ (nM) |
|---|---|---|---|
| B-3 | 2-fluorophenyl | 800 ± 400 | 49 |
| B-4 | 4-(trifluoromethoxy)phenyl | 8 ± 1 | 390 |
| B-5 | 4-methoxyphenyl | 130 ± 40 | 32 |
| B-6 | 3-pyridyl | 4700 ± 1800 | 14 |

Since substitution to the 4-methoxy increased potency towards sEH with a minor change in the potency towards FAAH, this leaving group was next used in combination with variations to the carbamoylating groups. Results are shown in Table 8 below. Modification of the 3-quinoline (B-5) to either the 2-quinoline (B-7) or the 3-phenyl-thiazole (B-10) resulted in a loss of potency towards both targets. Although the thiazole was modified from the thiadiazole, previous studies indicate this change does not impact potency towards FAAH. Additionally, modification to the 2-naphthylene (B-8) resulted in little change in potency towards either targets. Finally, modification to the 4-trifluoromethylpyridine-3-phenoxy (B-9) resulted in no change in potency towards sEH, with a 32-fold increase towards FAAH. This increase in potency is comparable to potencies previously reported.

TABLE 8

Effect of FAAH Carbamoylating Group on sEH Potency

| R²—L²— | | hsEH IC$_{50}$ (nM) | hFAAH K$_D$ (nM) | k$_2$ (min$^{-1}$) | K$_D$/k$_2$ (µM$^{-1}$ s$^{-1}$) |
|---|---|---|---|---|---|
| B-5 | 3-quinolinylmethyl | 130 ± 40 | 24 ± 4 | 0.37 ± 0.03 | 0.24 ± 0.04 |
| B-7 | 2-quinolinylmethyl | 680 ± 140 | 100 ± 40 | 0.28 ± 0.04 | 0.066 ± 0.023 |
| B-8 | 2-naphthylmethyl | 120 ± 30 | 18 ± 4 | 0.26 ± 0.03 | 0.26 ± 0.02 |
| B-9 | 4-trifluoromethylpyridine-3-phenoxy | 160 ± 20 | 0.70 ± 0.27 | 0.26 ± 0.03 | 6.8 ± 3.3 |

TABLE 8-continued

Effect of FAAH Carbamoylating Group on sEH Potency

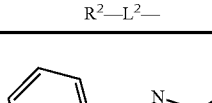

| | | hsEH | hFAAH | | |
|---|---|---|---|---|---|
| | $R^2-L^2-$ | $IC_{50}$ (nM) | $K_D$ (nM) | $k_2$ (min$^{-1}$) | $K_D/k_2$ (μM$^{-1}$ s$^{-1}$) |
| B-10 | [phenyl-thiazole-methyl] | 570 ± 170 | 750 ± 20 | 0.55 ± 0.02 | 0.012 ± 0.000 |

TABLE 9

Effect of FAAH Carbamoylating Group on sEH Potency

[structure with $R^2-L^2$ attached to piperidine carbamoyl 4-methoxyphenyl aniline]

| | $R^2-L^2-$ | hsEH $IC_{50}$ (nM) | hFAAH $IC_{50}$ (nM) |
|---|---|---|---|
| B-5 | [quinolin-3-ylmethyl] | 130 ± 40 | 32 |
| B-7 | [quinolin-2-ylmethyl] | 680 ± 140 | 34 |
| B-8 | [naphthalen-2-ylmethyl] | 120 ± 30 | 7.4 |
| B-9 | [5-(trifluoromethyl)pyridin-2-yloxy-3-ethylphenyl] | 160 ± 20 | 1.0 |
| B-10 | [4-phenyl-2-methylthiazol-5-ylmethyl] | 570 ± 170 | 250 |

Because the 4-trifluoromethoxy aniline was the primary determinant for sEH potency and the 2-(3-(piperidin-4-ylmethyl)phenoxy)-5-(trifluoromethyl)pyridine was the primary determinant for FAAH potency, both functionalities were combined in compound B-11 This afforded a molecule with single digit potency nM towards both sEH and FAAH. 4-Chloro-(B-12) and 4-trifluoromethyl-(B-13) analogs were compared to B-11, but neither improved potency. Since the unsubstituted pyridine improved potency on FAAH relative to the corresponding phenyl, 2- and 3-trifluoromethylpyridines (B-14 and B-15) were tested. While the potency on FAAH of 2-trifluoromethylpyridine (B-14) improved marginally compared to B-11, the potency on sEH decreased substantially as did potency on both sEH and FAAH towards the 3-trifluoromethylpyridine (B-15). Finally, substitution to the pyridazine (B-16) and 3,4-dimethylisoxazole (B-17) has previously increased potency towards FAAH; however, both substitutions dramatically decreased potency on sEH.

TABLE 10

Modification of Aryl leaving group with 2-(3-(piperidin-4-ylmethyl)phenoxy)-5-(trifluoromethyl)pyridine scaffold

[scaffold structure: $F_3C$-pyridine-O-phenyl-CH$_2$-piperidine-C(O)NH-$L^1$-$R^1$]

| | $-L^1-R^1$ | hsEH $IC_{50}$ (nM) | hFAAH $IC_{50}$ (nM) |
|---|---|---|---|
| B-11 | [4-OCF$_3$-phenyl] | 5 | 8 |
| B-12 | [4-Cl-phenyl] | 20 | 4 |
| B-13 | [4-CF$_3$-phenyl] | 7 | 8 |
| B-14 | [2-CF$_3$-pyridin-5-yl] | 60 | 3 |

TABLE 10-continued

Modification of Aryl leaving group with 2-(3-(piperidin-4-ylmethyl)phenoxy)-5-(trifluoromethyl)pyridine scaffold

| —L¹—R¹ | hsEH IC$_{50}$ (nM) | hFAAH IC$_{50}$ (nM) |
|---|---|---|
| B-15 | 70 | 24 |
| B-16 | >10,000 | 0.5 |
| B-17 | 500 | 1 |
| B-18 | 9 | 3 |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula J:

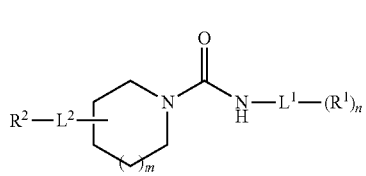

(J)

or a pharmaceutically acceptable salt or isomer thereof, wherein each R¹ is independently selected from the group consisting of hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)R$^{1a}$, —C(O)OR$^{1a}$, —OC(O)R$^{1a}$, —C(O)N(R$^{1a}$)(R$^{1b}$), —N(R$^{1b}$)C(O)R$^{1a}$, —C(O)N(R$^{1a}$)CH$_2$C(O)OR$^{1b}$, —N(R$^{1a}$)(R$^{1b}$), —S(O)$_2$R$^{1a}$, —S(O)$_2$N(R$^{1a}$)(R$^{1b}$), —N(R$^{1b}$)S(O)$_2$R$^{1a}$, $C_{3-8}$ cycloalkyl, $C_{5-10}$ heterocycloalkyl, $C_{6-12}$ aryl and $C_{5-12}$ heteroaryl;

R$^{1a}$ is selected from the group consisting of hydrogen, $C_{1-6}$ alkyl, $C_{1-6}$ hydroxyalkyl, and $C_{1-6}$ alkyl-$C_{6-12}$ aryl;

R$^{1b}$ is selected from the group consisting of hydrogen and $C_{1-6}$ alkyl;

L¹ is selected from the group consisting of $C_{6-10}$ arylene and $C_{5-10}$ heteroarylene;

L² is absent or $C_{1-6}$ alkylene;

R² is selected from the group consisting of $C_{6-12}$ aryl and $C_{5-12}$ heteroaryl, optionally substituted with 1 to 2 R$^{2a}$ groups;

each R$^{2a}$ is independently selected from the group consisting of hydrogen, $C_{6-12}$ aryl, —O—$C_{6-12}$ aryl, $C_{5-12}$ heteroaryl and —O—$C_{5-12}$ heteroaryl, wherein the $C_{6-12}$ aryl and $C_{5-12}$ heteroaryl groups are optionally substituted with 1 to 2 R$^{2b}$ groups;

each R$^{2b}$ is independently selected from the group consisting of halogen, $C_{1-6}$ haloalkyl, $C_{1-6}$ alkoxy and $C_{1-6}$ haloalkoxy;

subscript m is 1; and subscript n is an integer from 1 to 4;

provided that when R² is quinolin-3-yl, L² is methylene, subscripts m and n are both 1, and L¹ is phenylene, then R¹ is selected from the group consisting of $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)R$^{1a}$, —C(O)OR$^{1a}$, —OC(O)R$^{1a}$, —C(O)N(R$^{1a}$)(R$^{1b}$), —N(R$^{1b}$)C(O)R$^{1a}$, —C(O)N(R$^{1a}$)CH$_2$C(O)OR$^{1b}$, —N(R$^{1a}$)(R$^{1b}$), —S(O)$_2$R$^{1a}$, —S(O)$_2$N(R$^{1a}$)(R$^{1b}$), —N(R$^{1b}$)S(O)$_2$R$^{1a}$, $C_{3-8}$cycloalkyl, $C_{5-10}$ heterocycloalkyl, $C_{6-12}$ aryl and $C_{5-12}$ heteroaryl.

2. The compound of claim 1, wherein L¹ is selected from the group consisting of phenylene and $C_{5-6}$ heteroarylene.

3. The compound of claim 1, wherein L¹ is selected from the group consisting of phenylene and $C_{5-6}$ heteroarylene, wherein the heteroarylene comprises 1 to 2 heteroatoms each independently selected from the group consisting of N and O.

4. The compound of claim 1, wherein L¹ is selected from the group consisting of phenylene, pyridyl, pyridazinyl and isoxazolyl.

5. The compound of claim 1, wherein L¹ is selected from the group consisting of phenylene and pyridyl.

6. The compound of claim 1, according to Formula I

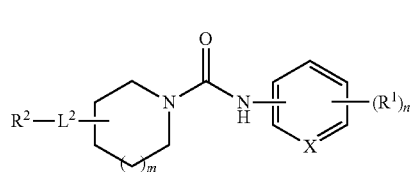

(I)

or a pharmaceutically acceptable salt or isomer thereof, wherein each R¹ is independently selected from the group consisting of hydrogen, $C_{1-6}$ alkyl, $C_{2-6}$ alkenyl, $C_{2-6}$ alkynyl, hydroxy, $C_{1-6}$ hydroxyalkyl, halogen, $C_{1-6}$ haloalkyl, $C_{1-6}$ alkoxy, $C_{1-6}$ haloalkoxy, —CN, —C(O)R$^{1a}$, —C(O)OR$^{1a}$, —OC(O)R$^{1a}$, —C(O)N(R$^{1a}$)(R$^{1b}$), —N(R$^{1b}$)C(O)R$^{1a}$, —C(O)N(R$^{1a}$)CH$_2$C(O)OR$^{1b}$, —N(R$^{1a}$)(R$^{1b}$), —S(O)$_2$R$^{1a}$, —S(O)$_2$N(R$^{1a}$)(R$^{1b}$), —N(R$^{1b}$)S(O)$_2$R$^{1a}$, C$_{3-8}$ cycloalkyl, C$_{5-10}$ heterocycloalkyl, C$_{6-12}$ aryl and C$_{5-12}$ heteroaryl;

R$^{1a}$ is selected from the group consisting of hydrogen, C$_{1-6}$ alkyl, C$_{1-6}$ hydroxyalkyl, and C$_{1-6}$ alkyl-C$_{6-12}$ aryl;

R$^{1b}$ is selected from the group consisting of hydrogen and C$_{1-6}$ alkyl;

L$^2$ is absent or C$_{1-6}$ alkylene;

R$^2$ is selected from the group consisting of C$_{6-12}$ aryl and C$_{5-12}$ heteroaryl, optionally substituted with 1 to 2 R$^{2a}$ groups;

each R$^{2a}$ is independently selected from the group consisting of hydrogen, C$_{6-12}$ aryl, —O—C$_{6-12}$ aryl, C$_{5-12}$ heteroaryl and —O—C$_{5-12}$ heteroaryl, wherein the C$_{6-12}$ aryl and C$_{5-12}$ heteroaryl groups are optionally substituted with 1 to 2 R$^{2b}$ groups;

each R$^{2b}$ is independently selected from the group consisting of halogen, C$_{1-6}$ haloalkyl, C$_{1-6}$ alkoxy and C$_{1-6}$ haloalkoxy;

X is selected from the group consisting of CH and N;

subscript m is 1; and subscript n is an integer from 1 to 4;

provided that when R$^2$ is quinolin-3-yl, L$^2$ is methylene, subscripts m and n are both 1, and X is CH, then R$^1$ is selected from the group consisting of C$_{1-6}$ alkyl, C$_{2-6}$ alkenyl, C$_{2-6}$ alkynyl, hydroxy, C$_{1-6}$ hydroxyalkyl, halogen, C$_{1-6}$ haloalkyl, C$_{1-6}$ alkoxy, C$_{1-6}$ haloalkoxy, —CN, —C(O)R$^{1a}$, —C(O)OR$^{1a}$, —OC(O)R$^{1a}$, —C(O)N(R$^{1a}$)(R$^{1b}$), —N(R$^{1b}$)C(O)R$^{1a}$, —C(O)N(R$^{1a}$)CH$_2$C(O)OR$^{1b}$, —N(R$^{1a}$)(R$^{12b}$), —S(O)$_2$R$^{1a}$, —S(O)$_2$N(R$^{1a}$)(R$^{1b}$), —N(R$^{1b}$)S(O)$_2$R$^{1a}$, C$_{3-8}$ cycloalkyl, C$_{5-10}$ heterocycloalkyl, C$_{6-12}$ aryl and C$_{5-12}$ heteroaryl.

7. The compound of claim 6, according to Formula Ia:

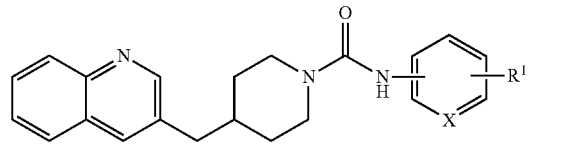
(Ia)

wherein

R$^1$ is selected from the group consisting of hydrogen, C$_{1-6}$ alkyl, hydroxy, C$_{1-6}$ hydroxyalkyl, halogen, C$_{1-6}$ haloalkyl, C$_{1-6}$ alkoxy, and C$_{1-6}$ haloalkoxy.

8. The compound of claim 7, wherein X is CH and R$^1$ is selected from the group consisting of halogen and C$_{1-6}$ alkoxy.

9. The compound of claim 7, wherein X is N and R$^1$ is hydrogen.

10. The compound of claim 7, which is selected from the group consisting of:

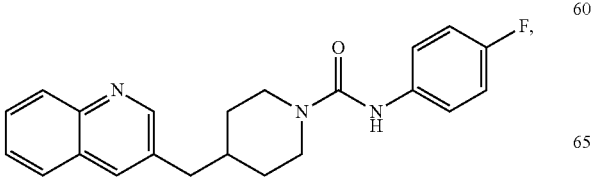

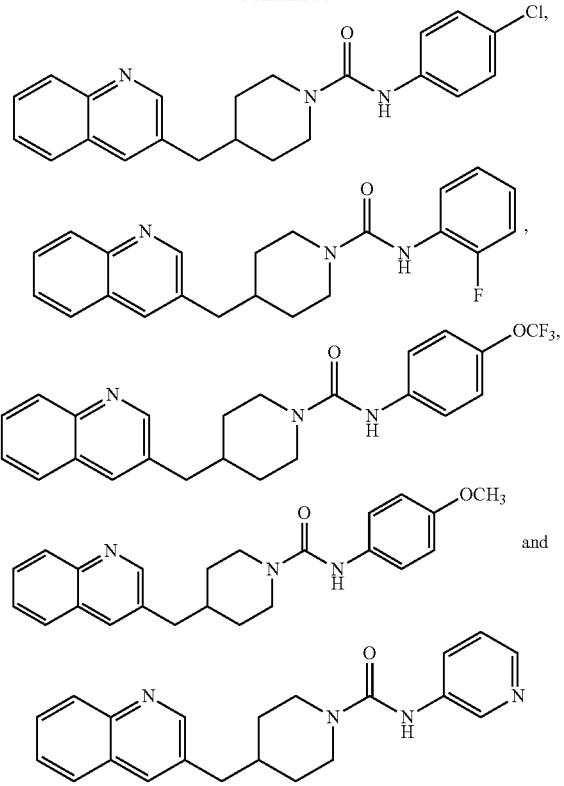

or a pharmaceutically acceptable salt or isomer thereof.

11. The compound of claim 6, according to Formula Ib:

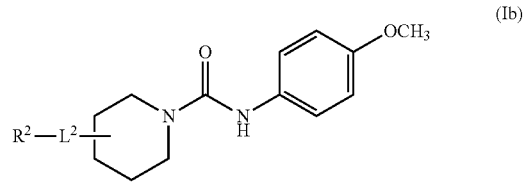
(Ib)

wherein

L$^2$ is absent or C$_{1-4}$ alkylene;

R$^2$ is selected from the group consisting of phenyl, naphthyl, pyridyl, quinolinyl, thiazolyl, imidazolyl, and triazolyl, each of which is optionally substituted with 1 R$^{2a}$ group;

R$^{2a}$ is selected from the group consisting of hydrogen, C$_{6-12}$ aryl, —O—C$_{6-12}$ aryl, and C$_{5-12}$ heteroaryl, wherein the C$_{6-12}$ aryl and C$_{5-12}$ heteroaryl groups are optionally substituted with 1 R$^{2b}$ group; and R$^{2b}$ is selected from the group consisting of halogen and C$_{1-6}$ haloalkyl.

12. The compound of claim 11, wherein

L$^2$ is methylene; and

R$^2$ is selected from the group consisting of naphthyl and quinolinyl, each of which is optionally substituted with 1 R$^{2a}$ group.

13. The compound of claim 11, wherein

L$^2$ is absent or methylene;

R$^2$ is selected from the group consisting of phenyl and thiazolyl, each of which is optionally substituted with 1 R$^{2a}$ group; and $R^{2a}$ is selected from the group consisting of phenyl and pyridyl, each of which is optionally substituted with 1 $C_{1-6}$ haloalkyl group.

14. The compound of claim 11, which is selected from the group consisting of:

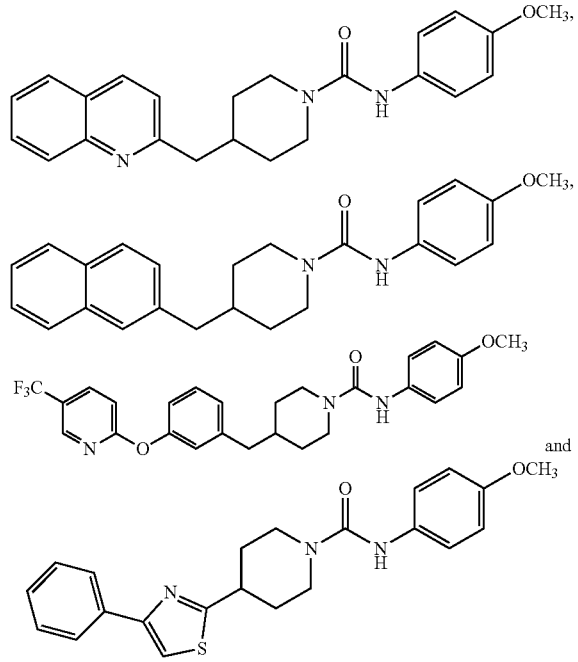

or a pharmaceutically acceptable salt or isomer thereof.

15. The compound of claim 6, according to Formula Ic:

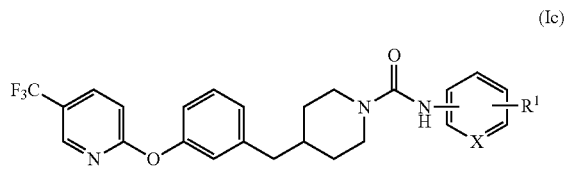

(Ic)

wherein
R¹ is selected from the group consisting of hydrogen, $C_{1-6}$ alkyl, hydroxy, $C_{1-6}$ hydroxyalkyl, halogen, $C_{1-6}$ haloalkyl, $C_{1-6}$ alkoxy, and $C_{1-6}$ haloalkoxy.

16. The compound of claim 15, which is selected from the group consisting of:

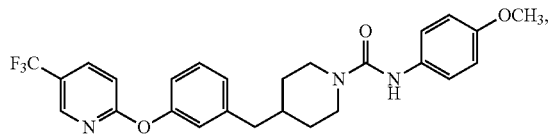

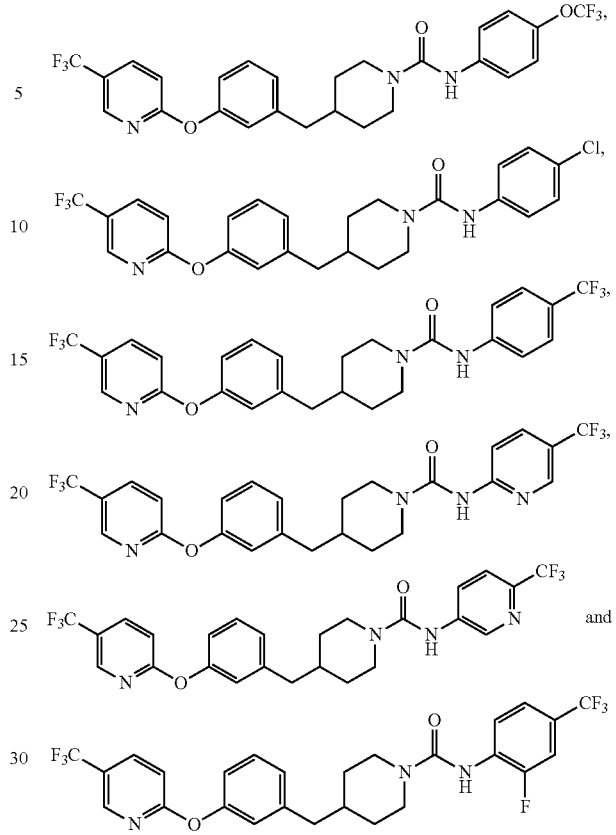

or a pharmaceutically acceptable salt or isomer thereof.

17. The compound of claim 1, which is selected from the group consisting of: f

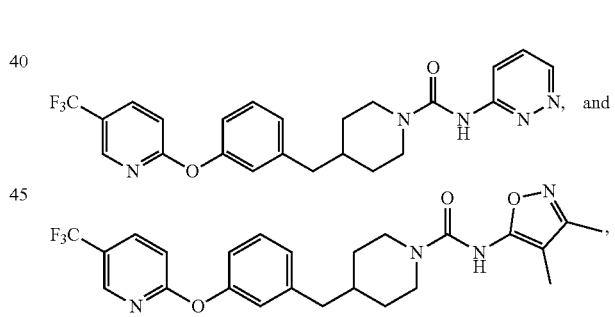

or a pharmaceutically acceptable salt or isomer thereof.

18. A method for inhibiting a soluble epoxide hydrolase and fatty acid amide hydrolase, the method comprising contacting the soluble epoxide hydrolase and fatty acid amide hydrolase with a therapeutically effective amount of a compound of claim 1 thereby inhibiting the soluble epoxide hydrolase and fatty acid amide hydrolase.

* * * * *